United States Patent
Hsu et al.

(10) Patent No.: US 11,117,964 B2
(45) Date of Patent: Sep. 14, 2021

(54) ANTI-KIR3DL1 ANTIBODIES

(71) Applicants: Memorial Sloan Kettering Cancer Center, New York, NY (US); Eureka Therapeutics, Inc., Emeryville, CA (US)

(72) Inventors: Katharine Hsu, New York, NY (US); Nai-Kong V. Cheung, New York, NY (US); Su Yan, Emeryville, CA (US); Yiyang Xu, Emeryville, CA (US); Jingyi Xiang, Emeryville, CA (US); Cheng Liu, Emeryville, CA (US)

(73) Assignees: MEMORIAL SLOAN KETTERING CANCER CENTER, New York, NY (US); EUREKA THERAPEUTICS, INC., Emeryville, CA (US)

( * ) Notice: Subject to any disclaimer, the term of this patent is extended or adjusted under 35 U.S.C. 154(b) by 116 days.

(21) Appl. No.: 16/484,451

(22) PCT Filed: Feb. 26, 2018

(86) PCT No.: PCT/US2018/017125
§ 371 (c)(1),
(2) Date: Aug. 7, 2019

(87) PCT Pub. No.: WO2018/148223
PCT Pub. Date: Aug. 16, 2018

(65) Prior Publication Data
US 2020/0031927 A1     Jan. 30, 2020

Related U.S. Application Data

(60) Provisional application No. 62/457,089, filed on Feb. 9, 2017.

(51) Int. Cl.
| | |
|---|---|
| C07K 16/28 | (2006.01) |
| A61K 39/295 | (2006.01) |
| A61P 35/02 | (2006.01) |
| G01N 33/53 | (2006.01) |
| C12N 5/10 | (2006.01) |
| C12N 15/63 | (2006.01) |
| C12N 15/11 | (2006.01) |
| A61K 47/68 | (2017.01) |
| A61K 39/395 | (2006.01) |
| A61K 45/06 | (2006.01) |
| C07K 14/705 | (2006.01) |

(52) U.S. Cl.
CPC ...... *C07K 16/2803* (2013.01); *A61K 39/3955* (2013.01); *A61K 45/06* (2013.01); *A61K 47/6849* (2017.08); *A61P 35/02* (2018.01); *C12N 5/10* (2013.01); *C12N 15/11* (2013.01); *C12N 15/63* (2013.01); *G01N 33/53* (2013.01); *C07K 14/70503* (2013.01); *C07K 2317/21* (2013.01); *C07K 2317/34* (2013.01); *C07K 2317/565* (2013.01); *C07K 2317/732* (2013.01); *C07K 2317/76* (2013.01); *C07K 2317/92* (2013.01)

(58) Field of Classification Search
CPC ............ C07K 16/2803; A61K 39/3955; A61P 35/02; G01N 33/53
See application file for complete search history.

(56) References Cited

U.S. PATENT DOCUMENTS

| | | | |
|---|---|---|---|
| 4,816,567 | A | 3/1989 | Cabilly et al. |
| 5,225,539 | A | 7/1993 | Winter |
| 5,580,990 | A | 12/1996 | Van Den Berg et al. |
| 5,660,827 | A | 8/1997 | Thorpe et al. |
| 5,670,356 | A | 9/1997 | Sherf et al. |
| 5,693,762 | A | 12/1997 | Queen et al. |
| 5,874,304 | A | 2/1999 | Zolotukhin et al. |
| 5,985,566 | A | 11/1999 | Houthoff et al. |
| 9,856,324 | B2 * | 1/2018 | Scholz ............... C07K 16/3084 |
| 2013/0251711 | A1 | 9/2013 | Andre et al. |

FOREIGN PATENT DOCUMENTS

| | | |
|---|---|---|
| WO | WO-2010/081890 A1 | 7/2010 |
| WO | WO-2010/141249 A2 | 12/2010 |
| WO | WO-2012/092539 A2 | 7/2012 |
| WO | WO-2015/037005 A1 | 3/2015 |

OTHER PUBLICATIONS

Sait et al (2017. Expert Rev Anticancer Ther. 17(10): 889-904; pp. 1-31 as printed).*
Bourdreau et al., "KIR3DL1 and HLA-B Density and Binding Calibrate NK Education and Response to HIV," J. Immunol., vol. 196, No. 8, pp. 3398-3410 (Apr. 15, 2016).
Forlenza et al., "KIR3DL1 Allelic Polymorphism and HLA-B Epitopes Modulate Response to Anti-GD2 Monoclonal Antibody in Patients with Neuroblastoma," J. Clin. Oncology, vol. 34, No. 21, pp. 2443-2451 (Jul. 20, 2016).
International Search Report and Written Opinion, PCT/US2018/017125, Memorial Sloan Kettering Cancer Center (dated Jul. 2, 2018).

* cited by examiner

*Primary Examiner* — Zachary C Howard
(74) *Attorney, Agent, or Firm* — Foley & Lardner LLP

(57) ABSTRACT

The disclosure provides antibody agents that bind to inhibitory human killer immunoglobulin-like receptors (KIRs). Particular antibody agents of the disclosure include antibody agents that bind to KIR3DL1 (also known as CD158e). Also provided are related nucleic acids, vectors, compositions and methods of using KIR-binding antibody agents of the present technology.

20 Claims, 6 Drawing Sheets
Specification includes a Sequence Listing.

ANTI-KIR3DL1 ANTIBODIES

CROSS-REFERENCE TO RELATED APPLICATIONS

This application is a National Stage Application of PCT/US2018/017125, filed Feb. 6, 2018, which claims the benefit of and priority to U.S. Provisional Application No. 62/457,089, filed Feb. 9, 2017, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Jan. 25, 2018, is named 115872-0350_SL.txt and is 41,100 bytes in size.

BACKGROUND

Natural killer (NK) cells are lymphocytes with innate anti-viral and anti-tumor capacity. Killer immunoglobulin-like receptor (KIR) family is a large group of polymorphic receptors expressed on NK cells, whose interaction with HLA class I ligands are important for NK cell function. There exists a need for compositions and methods that target KIRs.

SUMMARY

The present disclosure provides, at least in part, antibodies that bind to inhibitory killer immunoglobulin-like receptors (KIRs). For example, the disclosure provides antibody agents that target KIR3DL1 (also known as CD158e). In some embodiments, the antibody agent of the present technology binds to an inhibitory KIR and can block the KIR from engaging with its HLA ligand. In some embodiments, the antibody agent of the present technology binds to KIR3DL1 and blocks engagements (e.g., interactions) with a HLA-Bw4 ligand. In some embodiments, the antibody agent of the present technology binds to human KIR3DL1 on a natural killer cell (NK cell), wherein binding of the antibody agent activates the NK cell.

The present disclosure encompasses a recognition that, at least in certain patients, it may be beneficial to target particular subtypes and alleles of human KIRs. For example, the disclosure provides antibody agents that target human KIR3DL1. In some embodiments, the disclosure provides antibody agents that target one or more subtypes of human KIR3DL1. In some embodiments, the disclosure provides antibody agents that target particular alleles of human KIR3DL1. In some embodiments, the disclosure provides antibody agents that target one, two, three, four, five, six, seven, eight, nine, ten or more alleles of human KIR3DL1. In some embodiments, the KIR3DL1 antibody agent of the present technology can bind to one or more alleles of human KIR3DL1 selected from: *001, *016, *026, *027, *043, *052, *059, *060, *061, *064, *065, *067, *075, *002, *015, *008, *009, *020, *006, *017, *018, *022, *023, *024N, *025, *028, *029, *030, *031, *034, *035, *038, *042, *051, *054, *057, *062, *067, *074, *076, *077, *005, *041, *044, *053, *007, *032, *030, *068, *013, *010, *011, *012, *014, *045, *046, *047, *048, *049N, *050, *055, *058, *073, *004, *019, *021, *036, *037, *039, *040, *056, *063, and *072. In some embodiments, the KIR3DL1 antibody agent can bind to one or more alleles of human KIR3DL1, such as KIR3DL1*001, *002,*007, *015, *020, and/or *033. In some embodiments, the KIR3DL1 antibody agent is conjugated to a payload selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof.

In some embodiments, the KIR antibody agent is a human antibody that binds to human KIR3DL1. In some embodiments, the KIR antibody agent is a humanized antibody that binds to human KIR3DL1. In some embodiments, the KIR antibody agent is a chimeric antibody that binds to human KIR3DL1.

In some embodiments, the KIR antibody agent comprises a heavy chain variable region with one or more CDR sequences selected from SEQ ID NOs: 23, 24, 25, 29, 30, 31, 35, 36, 37, 41, 42, 43, 47, 48, 49, 53, 54, 55, 59, 60 and 61 and/or a light chain variable region with one or more CDR sequences selected from SEQ ID NOs: 20, 21, 22, 26, 27, 28, 32, 33, 34, 38, 39, 40, 44, 45, 46, 50, 51, 52, 56, 57, and 58. In some embodiments, the KIR antibody agent comprises a heavy chain variable region with two or more CDR sequences selected from SEQ ID NOs: 23, 24, 25, 29, 30, 31, 35, 36, 37, 41, 42, 43, 47, 48, 49, 53, 54, 55, 59, 60 and 61 and/or a light chain variable region with two or more CDR sequences selected from SEQ ID NOs: 20, 21, 22, 26, 27, 28, 32, 33, 34, 38, 39, 40, 44, 45, 46, 50, 51, 52, 56, 57, and 58. In some embodiments, the KIR antibody agent comprises a heavy chain variable region with three or more CDR sequences selected from SEQ ID NOs: 23, 24, 25, 29, 30, 31, 35, 36, 37, 41, 42, 43, 47, 48, 49, 53, 54, 55, 59, 60 and 61 and/or a light chain variable region with three or more CDR sequences selected from SEQ ID NOs: 20, 21, 22, 26, 27, 28, 32, 33, 34, 38, 39, 40, 44, 45, 46, 50, 51, 52, 56, 57, and 58.

In some embodiments, the KIR antibody agent comprises a heavy chain variable region with one or more CDR sequences as set forth in SEQ ID NOs: 23, 24, 25, 29, 30, 31, 35, 36, 37, 41, 42, 43, 47, 48, 49, 53, 54, 55, 59, 60 or 61, or a corresponding sequence containing 1, 2, 3, 4, or 5 amino acid substitutions. In some embodiments, the KIR antibody agent comprises a light chain variable region with one or more CDR sequences as set forth in SEQ ID NOs: 20, 21, 22, 26, 27, 28, 32, 33, 34, 38, 39, 40, 44, 45, 46, 50, 51, 52, 56, 57, or 58 or a corresponding sequence containing 1, 2, 3, 4, or 5 amino acid substitutions.

In some embodiments, the KIR antibody agent comprises a heavy chain variable region with the three CDRs, as set forth in Table 1. In some embodiments, the KIR antibody agent comprises a light chain variable region with the three CDRs, as set forth in Table 1.

In some embodiments, the KIR antibody agent comprises a heavy chain variable region with three CDRs, wherein heavy chain CDR1 comprises a sequence as set forth in SEQ ID NO:23, heavy chain CDR2 comprises a sequence as set forth in SEQ ID NO:24 and heavy chain CDR3 comprises a sequence as set forth in SEQ ID NO:25. In some embodiments, the KIR antibody agent comprises a light chain variable region with three CDRs, wherein light chain CDR1 comprises a sequence as set forth in SEQ ID NO:20, light chain CDR2 comprises a sequence as set forth in SEQ ID NO:21 and light chain CDR3 comprises a sequence as set forth in SEQ ID NO:22.

In some embodiments, the KIR antibody agent comprises a heavy chain variable region with three CDRs, wherein heavy chain CDR1 comprises a sequence as set forth in SEQ ID NO:29, heavy chain CDR2 comprises a sequence as set forth in SEQ ID NO:30 and heavy chain CDR3 comprises a sequence as set forth in SEQ ID NO:31. In some embodiments, the KIR antibody agent comprises a light chain variable region with three CDRs, wherein light chain CDR1 comprises a sequence as set forth in SEQ ID NO:26, light chain CDR2 comprises a sequence as set forth in SEQ ID NO:27 and light chain CDR3 comprises a sequence as set forth in SEQ ID NO:28.

In some embodiments, the KIR antibody agent comprises a heavy chain variable region with three CDRs, wherein heavy chain CDR1 comprises a sequence as set forth in SEQ ID NO:35, heavy chain CDR2 comprises a sequence as set forth in SEQ ID NO:36 and heavy chain CDR3 comprises a sequence as set forth in SEQ ID NO:37. In some embodiments, the KIR antibody agent comprises a light chain variable region with three CDRs, wherein light chain CDR1 comprises a sequence as set forth in SEQ ID NO: 32, light chain CDR2 comprises a sequence as set forth in SEQ ID NO:33 and light chain CDR3 comprises a sequence as set forth in SEQ ID NO:34.

In some embodiments, the KIR antibody agent comprises a heavy chain variable region with three CDRs, wherein heavy chain CDR1 comprises a sequence as set forth in SEQ ID NO:41, heavy chain CDR2 comprises a sequence as set forth in SEQ ID NO:42 and heavy chain CDR3 comprises a sequence as set forth in SEQ ID NO:43. In some embodiments, the KIR antibody agent comprises a light chain variable region with three CDRs, wherein light chain CDR1 comprises a sequence as set forth in SEQ ID NO:38, light chain CDR2 comprises a sequence as set forth in SEQ ID NO:39 and light chain CDR3 comprises a sequence as set forth in SEQ ID NO:40.

In some embodiments, the KIR antibody agent comprises a heavy chain variable region with three CDRs, wherein heavy chain CDR1 comprises a sequence as set forth in SEQ ID NO:47, heavy chain CDR2 comprises a sequence as set forth in SEQ ID NO:48 and heavy chain CDR3 comprises a sequence as set forth in SEQ ID NO:49. In some embodiments, the KIR antibody agent comprises a light chain variable region with three CDRs, wherein light chain CDR1 comprises a sequence as set forth in SEQ ID NO:44, light chain CDR2 comprises a sequence as set forth in SEQ ID NO:45 and light chain CDR3 comprises a sequence as set forth in SEQ ID NO:46.

In some embodiments, the KIR antibody agent comprises a heavy chain variable region with three CDRs, wherein heavy chain CDR1 comprises a sequence as set forth in SEQ ID NO:53, heavy chain CDR2 comprises a sequence as set forth in SEQ ID NO:54 and heavy chain CDR3 comprises a sequence as set forth in SEQ ID NO:55. In some embodiments, the KIR antibody agent comprises a light chain variable region with three CDRs, wherein light chain CDR1 comprises a sequence as set forth in SEQ ID NO:50, light chain CDR2 comprises a sequence as set forth in SEQ ID NO:51 and light chain CDR3 comprises a sequence as set forth in SEQ ID NO:52.

In some embodiments, the KIR antibody agent comprises a heavy chain variable region with three CDRs, wherein heavy chain CDR1 comprises a sequence as set forth in SEQ ID NO:59, heavy chain CDR2 comprises a sequence as set forth in SEQ ID NO:60 and heavy chain CDR3 comprises a sequence as set forth in SEQ ID NO:61. In some embodiments, the KIR antibody agent comprises a light chain variable region with three CDRs, wherein light chain CDR1 comprises a sequence as set forth in SEQ ID NO:56, light chain CDR2 comprises a sequence as set forth in SEQ ID NO:57 and light chain CDR3 comprises a sequence as set forth in SEQ ID NO:58.

In some embodiments, the KIR antibody agent comprises a heavy chain variable region having a sequence selected from SEQ ID NOs: 7, 9, 11, 13, 15, 17, and 19; and/or a light chain variable region having a sequence selected from SEQ ID NOs: 6, 8, 10, 12, 14, 16, and 18.

In some embodiments, a KIR3DL1 antibody agent comprises a heavy chain variable region and a light chain variable region wherein the heavy chain variable region has a sequence that is at least about 70% (e.g., at least about 70%, 75%, 80%, 85%, 90%, 95%, 96%, 97%, 98%, or 99%) identical to any one of SEQ ID NO: 7, 9, 11, 13, 15, 17, and 19 and wherein the light chain variable region has a sequence that is at least about 70% (e.g., at least about 70%, 75%, 80%, 85%, 90%, 95%, 96%, 97%, 98%, or 99%) identical to any one of SEQ ID NO: 6, 8, 10, 12, 14, 16, and 18.

In some embodiments, the KIR antibody agent is or comprises a human monoclonal antibody or an antigen binding fragment thereof. In some embodiments, the KIR antibody agent is a human KIR3DL1 monoclonal antibody. In some embodiments, the KIR antibody agent is or comprises an IgG1 region. In some embodiments, the KIR antibody agent is an antigen binding fragment selected from the group consisting of Fab, $F(ab')_2$, Fab', $scF_v$, $F_v$, and VH. In some embodiments, the KIR antibody agent is an antigen binding fragment selected from the group consisting of Fab, $F(ab')_2$, Fab', $scF_v$, $F_v$ and VH that specifically binds to KIR3DL1.

The present disclosure also provides isolated nucleic acid molecules that encode, in whole or in part, the KIR antibody agent (e.g., an agent that encodes KIR3DL1) and recombinant vectors encoding the same. Also provided are host cells comprising recombinant vectors or nucleic acids encoding KIR antibody agents (e.g., KIR3DL1 antibody agents). Host cells may include bacterial, yeast, insect and mammalian cells. In some embodiments, a host cell may be selected from the group consisting of *E. coli, P. pastoris*, Sf9, COS, HEK293, CHO and a mammalian lymphocyte. In some embodiments, the mammalian lymphocyte is a human lymphocyte.

The present disclosure provides methods of treating cancer in a subject in need thereof comprising administering to the subject a therapeutically effective amount of a composition that comprises and/or delivers the KIR antibody agent (e.g., a KIR3DL1 antibody agent, nucleic acid encoding the same, or a recombinant vector comprising the same) of the present technology. In some embodiments, the composition is administered orally, intranasally, parenterally, intravenously, intramuscularly, intraperitoneally, subcutaneously, rectally, intrathecally, intratumorally or topically.

In some embodiments are provided uses of KIR antibody agents. In some embodiments, KIR antibody agents are for use in medicine (e.g., pharmaceutical composition). In some embodiments, KIR antibody agents are for use in treating a subject that has or is at risk for developing cancer. In some embodiments, a cancer may be or comprise a blood cancer (e.g., a leukemia); in some embodiments, a cancer is acute myeloid leukemia (AML). In some embodiments, a cancer may be or comprise one or more solid tumors; examples of such cancers include, e.g., neuroblastoma.

In some embodiments, a subject to whom the KIR antibody agent is to be administered comprises an allele of KIR3DL1. In some embodiments, a subject to whom the KIR antibody agent is to be administered may express an allele of KIR3DL1. In some embodiments, a KIR3DL1 allele (and/or expression thereof) may be detected in a sample obtained from the subject. In some embodiments, the sample is a tissue or blood sample. In some embodiments, a sample may comprise nucleic acids and/or protein. In some embodiments, a KIR3DL1 allele nucleic acid (e.g., DNA and/or RNA) is detected; in some embodiments, a KIR3DL1 allele polypeptide is detected. In some embodiments, a KIR3DL1 allele nucleic acid (e.g., polynucleotide encoding the KIR3DL1 allele, and/or its complement) is detected in a sample that comprises genomic DNA.

In some embodiments, a subject in need thereof has received, is receiving, and/or will receive at least one other therapy in addition to provided therapy with a KIR antibody agent as described herein, so that the subject is receiving the therapies in combination. The at least one other therapy may be administered separately, sequentially or simultaneously. In some embodiments, such other therapy may enhance ADCC activity, such as may occur, for example, upon administration of an agent such as, for example, rituximab (Rituxan™), trastuzumab (Herceptin®), cetuximab, anti-CD38, anti-GD2, Granulocyte/macrophage-colony stimulating factor (GM-CSF), IFN-α, IFN-β, IL-2, IL-12, IL-15, IL-21, anti-GITR, anti-CD47 and/or anti-PD-1. In some embodiments, such other therapy may be or comprise anti-GD2 immunotherapy (e.g., administration of an antibody agent that targets GD-2). In some embodiments, a subject that is suffering from or susceptible to cancer will receive treatment with a KIR antibody agent of the present technology and at least one additional therapy for enhancing ADCC, such as, for example, rituximab (Rituxan™), trastuzumab (Herceptin®), cetuximab, anti-CD38, anti-GD2, GM-CSF, IFN-α, IFN-β, IL-2, IL-12, IL-15, IL-21, anti-GITR, anti-CD47 and/or anti-PD-1.

In some embodiments, provided KIR antibody agents are useful and/or are used in manufacture of a pharmaceutical composition. In some embodiments, a pharmaceutical composition comprises a KIR antibody agent of the present technology (e.g., a KIR3DL1 antibody agent) and a pharmaceutically acceptable carrier. Also provided are methods of manufacturing pharmaceutical compositions; in some embodiments, such methods may comprise steps of combining the KIR antibody agent with a pharmaceutically acceptable carrier and/or formulating such a combination for administration to a subject. In some embodiments, a pharmaceutical composition is formulated for parenteral delivery. In some embodiments, a pharmaceutical composition is for treatment of cancer (e.g., AML or neuroblastoma).

Also disclosed herein are kits comprising at least one antibody agent of the present technology (e.g., any antibody or antigen binding fragment described herein), or a functional variant (e.g., substitutional variant) thereof and instructions for use. In certain embodiments, the antibody agent is coupled to one or more detectable labels. In one embodiment, the one or more detectable labels comprise a radioactive label, a fluorescent label, or a chromogenic label. Additionally or alternatively, in some embodiments, the kit further comprises a secondary antibody that specifically binds to an antibody agent described herein. In some embodiments, the secondary antibody is coupled to at least one detectable label selected from the group consisting of a radioactive label, a fluorescent label, or a chromogenic label.

BRIEF DESCRIPTION OF THE DRAWINGS

FIG. 5A shows 3F8 ADCC activation of NK expressing different 3DL1 subtypes and subsequent NK disinhibition in the presence of anti-HLA or DX9 blocking monoclonal antibodies (mAbs). FIG. 5B shows 3F8 ADCC NK activation against BelN in the presence of human IgG1 anti-KIR3DL1 mAbs of the present technology or DX9.

DETAILED DESCRIPTION

Definitions

Figure 1:
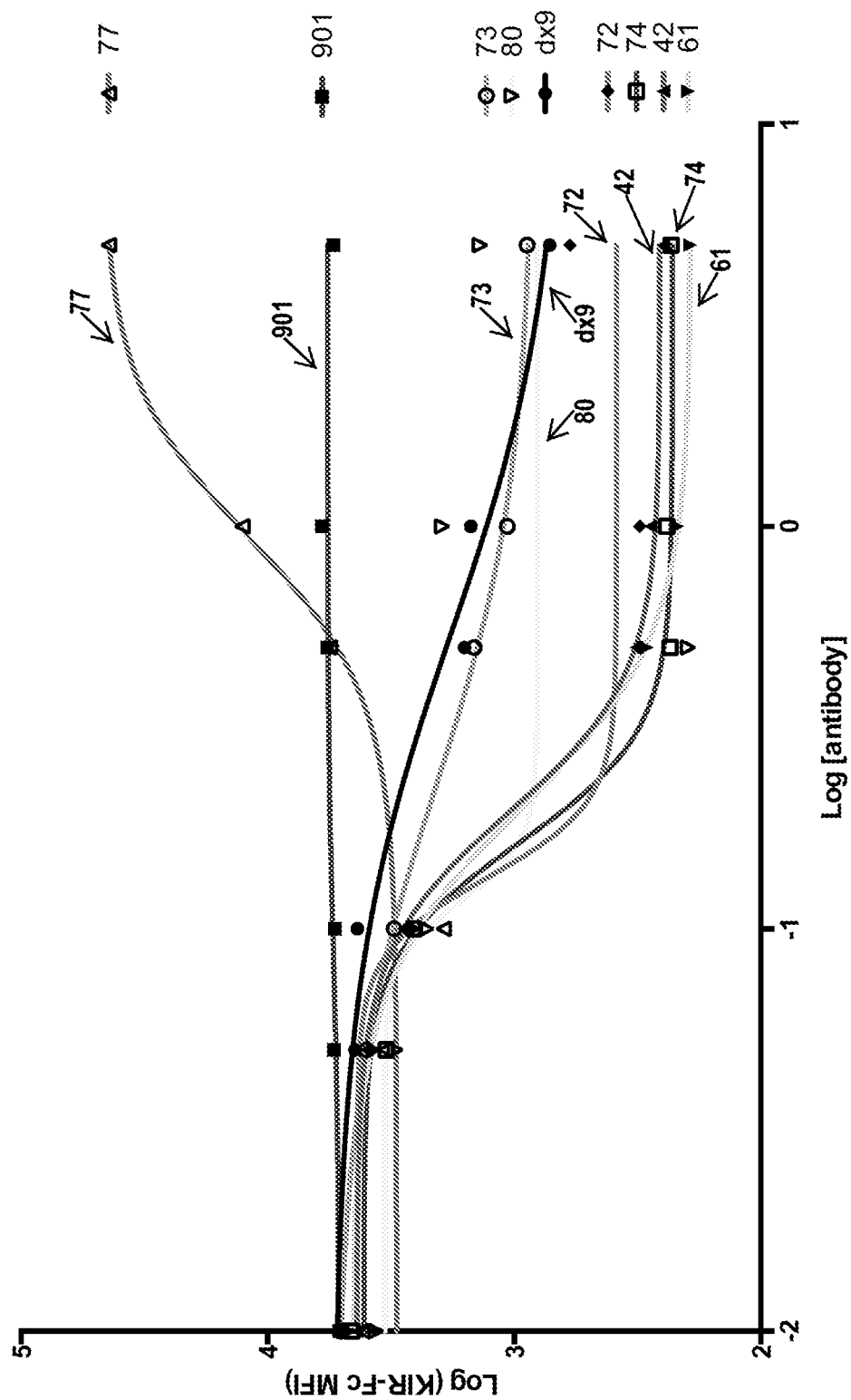
FIG. 1 depicts the binding profiles of various antibody candidates of the present technology to soluble KIR3DL1-Fc constructs. Human IgG1 anti-KIR3DL1 antibody candidates (ET160-42, ET160-61, ET160-72, ET160-73, ET160-74, ET160-77 and ET160-80) were tested at increasing concentrations for their ability to compete with binding of soluble KIR3DL1-Fc binding to a Bw4+ transfectant. The binding profiles of the non-specific control antibody 901 and the murine anti-KIR3DL1 antibody DX9 are shown for comparison.

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Administration: As used herein, the term "administration" typically refers to the administration of a composition to a subject or system to achieve delivery of an agent that is, or is included in, the composition. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e.g., intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time. Administration includes self-administration and the administration by another.

Affinity: As is known in the art, "affinity" is a measure of the tightness with which a particular ligand binds to its partner. Affinities can be measured in different ways. In some embodiments, affinity is measured by a quantitative assay. In some embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

Allele: As used herein, the term "allele" refers to one of two or more existing genetic variants of a specific polymorphic genomic locus.

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprising two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y structure's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Those skilled in the art are well familiar with antibody structure and sequence elements, recognize "variable" and "constant" regions in provided sequences, and understand that there may be some flexibility in definition of a "boundary" between such domains such that different presentations of the same antibody chain sequence may, for example, indicate such a boundary at a location that is shifted one or a few residues relative to a different presentation of the same antibody chain sequence. Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present disclosure include glycosylated Fc domains, including Fc domains with modified or engineered such glycosylation. For purposes of the present disclosure, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc., as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present disclosure is in a format selected from, but not limited to, intact IgA, IgG, IgE or IgM antibodies; bi- or multi-specific antibodies (e.g., Zybodies®, etc.); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Transbodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc.], or other pendant group [e.g., poly-ethylene glycol, etc.]

Antibody agent: As used herein, the term "antibody agent" refers to an agent that specifically binds to a particular antigen and encompasses any polypeptide or polypeptide complex that includes immunoglobulin structural elements sufficient to confer specific binding e.g., an antibody or an antigen binding fragment thereof (e.g., KIR antibody agent). Exemplary antibody agents include monoclonal antibodies or polyclonal antibodies. In some embodiments, an antibody agent may include one or more constant region sequences that are characteristic of mouse, rabbit, primate, or human antibodies. In some embodiments, an antibody agent may include one or more sequence elements are humanized, primatized, chimeric, etc., as is known in the art. In many embodiments, the term "antibody agent" is used to refer to one or more of the art-known or developed constructs or formats for utilizing antibody structural and functional features in alternative presentation. For example, embodiments, an antibody agent utilized in accordance with the present disclosure is in a format selected from, but not limited to, intact IgA, IgG, IgD, IgE or IgM antibodies; bi- or multi-specific antibodies (e.g., Zybodies®, etc.); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc.], or other pendant group [e.g., poly-ethylene glycol, etc.]. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

Antibody-Dependent Cellular Cytotoxicity: As used herein, the term "antibody-dependent cellular cytotoxicity" or "ADCC" refers to a phenomenon in which target cells bound by antibody are killed by immune effector cells. Without wishing to be bound by any particular theory, ADCC is typically believed to involve Fc receptor (FcR)-bearing effector cells that can recognize and subsequently kill antibody-coated target cells (e.g., cells that express on their surface specific antigens to which an antibody is bound). Effector cells that mediate ADCC can include immune cells, including but not limited to one or more of natural killer (NK) cells, macrophage, neutrophils, eosinophils.

Antigen: The term "antigen", as used herein, refers to an agent that elicits an immune response; and/or (ii) an agent that binds to a T cell receptor (e.g., when presented by an MHC molecule) or to an antibody. In some embodiments, an antigen elicits a humoral response (e.g., including production of antigen-specific antibodies); in some embodiments, an antigen elicits a cellular response (e.g., involving T-cells whose receptors specifically interact with the antigen). In some embodiments, an antigen binds to an antibody and may or may not induce a particular physiological response in an organism. In general, an antigen may be or include any chemical entity such as, for example, a small molecule, a nucleic acid, a polypeptide, a carbohydrate, a lipid, a polymer (in some embodiments other than a biologic polymer [e.g., other than a nucleic acid or amino acid polymer) etc. In some embodiments, an antigen is or comprises a polypeptide. In some embodiments, an antigen is or comprises a glycan. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source). In some embodiments, antigens utilized in accordance with the present disclosure are provided in a crude form. In some embodiments, an antigen is a recombinant antigen.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

Binding agent: In general, the term "binding agent" is used herein to refer to any entity that binds to a target of interest as described herein. In many embodiments, a binding agent of interest is one that binds specifically with its target in that it discriminates its target from other potential binding partners in a particular interaction context. In general, a binding agent may be or comprise an entity of any chemical class (e.g., polymer, non-polymer, small molecule, polypeptide, carbohydrate, lipid, nucleic acid, etc.). In some embodiments, a binding agent is a single chemical entity. In some embodiments, a binding agent is a complex of two or more discrete chemical entities associated with one another under relevant conditions by non-covalent interactions. For example, those skilled in the art will appreciate that in some embodiments, a binding agent may comprise a "generic" binding moiety (e.g., one of biotin/avidin/streptavidin and/or a class-specific antibody) and a "specific" binding moiety (e.g., an antibody or aptamers with a particular molecular target) that is linked to the partner of the generic binding moiety. In some embodiments, such an approach can permit modular assembly of multiple binding agents through linkage of different specific binding moieties with the same generic binding moiety partner. In some embodiments, binding agents are or comprise polypeptides (including, e.g., antibodies or antibody fragments). In some embodiments, binding agents are or comprise small molecules. In some embodiments, binding agents are or comprise nucleic acids. In some embodiments, binding agents are aptamers. In some embodiments, binding agents are polymers; in some embodiments, binding agents are not polymers. In some embodiments, binding agents are non-polymeric in that they lack polymeric moieties. In some embodiments, binding agents are or comprise carbohydrates. In some embodiments, binding agents are or comprise lectins. In some embodiments, binding agents are or comprise peptidomimetics. In some embodiments, binding agents are or comprise scaffold proteins. In some embodiments, binding agents are or comprise mimotopes. In some embodiments, binding agents are or comprise nucleic acids, such as DNA or RNA.

Biologically active: as used herein, refers to an observable biological effect or result achieved by an agent or entity of interest. For example, in some embodiments, a specific binding interaction is a biological activity. In some embodiments, modulation (e.g., induction, enhancement, or inhibition) of a biological pathway or event is a biological activity. In some embodiments, the presence or extent of a biological activity is assessed through detection of a direct or indirect product produced by a biological pathway or event of interest.

Bispecific antibody: as used herein, refers to a bispecific binding agent in which at least one, and typically both, of the binding moieties comprises an antibody component. A variety of different bi-specific antibody structures are known in the art. In some embodiments, each binding moiety in a bispecific antibody that is or comprises an antibody component includes $V_H$ and/or $V_L$ regions; in some such embodiments, the $V_H$ and/or $V_L$ regions are those found in a particular monoclonal antibody. In some embodiments, where the bispecific antibody contains two antibody component-binding moieties, each includes $V_H$ and/or $V_L$ regions from different monoclonal antibodies. In some embodiments, where the bispecific antibody contains two antibody component binding moieties, wherein one of the two antibody component binding moieties includes an immunoglobulin molecule having $V_H$ and/or $V_L$ regions that contain CDRs from a first monoclonal antibody, and one of the two antibody component binding moieties includes an antibody fragment (e.g., Fab, F(ab'), F(ab')$_2$, Fd, Fv, dAB, scFv, etc.) having $V_H$ and/or $V_L$ regions that contain CDRs from a second monoclonal antibody.

Bispecific binding agent: as used herein, refers to a polypeptide agent with two discrete binding moieties, each of which binds with a distinct target. In some embodiments, a bispecific binding agent is or comprises a single polypeptide; in some embodiments, a bispecific binding agent is or comprises a plurality of peptides which, in some such embodiments may be covalently associated with one another, for example by cross-linking. In some embodiments, the two binding moieties of a bispecific binding agent recognize different sites (e.g., epitopes) within the same target (e.g., antigen); in some embodiments, the two binding moieties of a bispecific binding agent recognize different targets. In some embodiments, a bispecific binding agent is capable of binding simultaneously to two targets that are of different structure.

Cancer: The terms "cancer", "malignancy", "neoplasm", "tumor", and "carcinoma", are used herein to refer to cells that exhibit relatively abnormal, uncontrolled, and/or autonomous growth, so that they exhibit an aberrant growth phenotype characterized by a significant loss of control of cell proliferation. In some embodiments, a tumor may be or comprise cells that are precancerous (e.g., benign), malignant, pre-metastatic, metastatic, and/or non-metastatic. The present disclosure specifically identifies certain cancers to which its teachings may be particularly relevant. In some embodiments, a relevant cancer may be characterized by a solid tumor. In some embodiments, a relevant cancer may be characterized by a hematologic tumor. In general, examples of different types of cancers known in the art include, for example, hematopoietic cancers including leukemias, lymphomas (Hodgkin's and non-Hodgkin's), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like.

Carrier: as used herein, refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

Combination therapy: As used herein, the term "combination therapy" refers to a clinical intervention in which a subject is simultaneously exposed to two or more therapeutic regimens (e.g., two or more therapeutic agents). In some embodiments, the two or more therapeutic regimens may be administered simultaneously. In some embodiments, the two or more therapeutic regimens may be administered sequentially (e.g., a first regimen administered prior to administration of any doses of a second regimen). In some embodiments, the two or more therapeutic regimens are administered in overlapping dosing regimens. In some embodiments, administration of combination therapy may involve administration of one or more therapeutic agents or modalities to a subject receiving the other agent(s) or modality. In some embodiments, combination therapy does not necessarily require that individual agents be administered together in a single composition (or even necessarily at the same time). In some embodiments, two or more therapeutic agents or modalities of a combination therapy are administered to a subject separately, e.g., in separate compositions, via separate administration routes (e.g., one agent orally and another agent intravenously), and/or at different time points. In some embodiments, two or more therapeutic agents may be administered together in a combination composition, or even in a combination compound (e.g., as part of a single chemical complex or covalent entity), via the same administration route, and/or at the same time.

Composition: Those skilled in the art will appreciate that the term "composition", as used herein, may be used to refer to a discrete physical entity that comprises one or more specified components. In general, unless otherwise specified, a composition may be of any form—e.g., gas, gel, liquid, solid, etc.

Corresponding to: As used herein, the term "corresponding to" may be used to designate the position/identity of a structural element in a compound or composition through comparison with an appropriate reference compound or composition. For example, in some embodiments, a monomeric residue in a polymer (e.g., an amino acid residue in a polypeptide or a nucleic acid residue in a polynucleotide) may be identified as "corresponding to" a residue in an appropriate reference polymer. For example, those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the $190^{th}$ amino acid in a particular amino acid chain but rather corresponds to the residue found at position 190 in the reference polypeptide; those of ordinary skill in the art readily appreciate how to identify "corresponding" amino acids. For example, those skilled in the art will be aware of various sequence alignment strategies, including software programs such as, for example, BLAST, CS-BLAST, CUSASW++, DIAMOND, FASTA, GGSEARCH/GLSEARCH, Genoogle, HMMER, HHpred/HHsearch, IDF, Infernal, KLAST, USEARCH, parasail, PSI-BLAST, PSI-Search, ScalaBLAST, Sequilab, SAM, SSEARCH, SWAPHI, SWAPHI-LS, SWIMM, or SWIPE that can be utilized, for example, to identify "corresponding" residues in polypeptides and/or nucleic acids in accordance with the present disclosure.

Dosing regimen: Those skilled in the art will appreciate that the term "dosing regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen). In some embodiments, a regimen comprises at least one dose, wherein the dose comprises one unit dose of a therapeutic agent (e.g., a KIR3DL1 antibody agent). In some embodiments, a regimen comprises at least one dose, wherein the dose comprises two or more unit doses of a therapeutic agent. For example, a dose of 500 mg can be administered as a single 500 mg unit dose or as two 250 mg unit doses. In some embodiments, a regimen is correlated with results in a desired or beneficial outcome when administered across a relevant population (i.e., is a therapeutic regimen).

Effector function: as used herein refers to a biochemical event that results from the interaction of an antibody Fc region with an Fc receptor or ligand. Effector functions include but are not limited to antibody-dependent cell-mediated cytotoxicity (ADCC), antibody-dependent cell-mediated phagocytosis (ADCP), and complement-mediated cytotoxicity (CMC). In some embodiments, an effector function is one that operates after the binding of an antigen, one that operates independent of antigen binding, or both.

Epitope: as used herein, includes any moiety that is specifically recognized by an immunoglobulin (e.g., antibody or receptor) binding component. In some embodiments, an epitope is comprised of a plurality of chemical atoms or groups on an antigen. In some embodiments, such chemical atoms or groups are surface-exposed when the antigen adopts a relevant three-dimensional conformation. In some embodiments, such chemical atoms or groups are physically near to each other in space when the antigen adopts such a conformation. In some embodiments, at least some such chemical atoms are groups are physically separated from one another when the antigen adopts an alternative conformation (e.g., is linearized).

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 50%, 55%, 60%, 65%, 70%, 75%, 80%, 85%, 90%, 95%, or 99% identical. In some embodiments, polymeric molecules are considered to be "homologous" to one another if their sequences are at least 50%, 55%, 60%, 65%, 70%, 75%, 80%, 85%, 90%, 95%, or 99% similar (e.g., containing residues with related chemical properties at corresponding positions). For example, as is well known by those of ordinary skill in the art, certain amino acids are typically classified as similar to one another as "hydrophobic" or "hydrophilic" amino acids, and/or as having "polar" or "non-polar" side chains. Substitution of one amino acid for another of the same type may often be considered a "homologous" substitution. Typical amino acid categorizations are summarized below:

| Alanine | Ala | A | nonpolar | neutral | 1.8 |
| Arginine | Arg | R | polar | positive | -4.5 |
| Asparagine | Asn | N | polar | neutral | -3.5 |
| Aspartic acid | Asp | D | polar | negative | -3.5 |
| Cysteine | Cys | C | nonpolar | neutral | 2.5 |
| Glutamic acid | Glu | E | polar | negative | -3.5 |
| Glutamine | Gln | Q | polar | neutral | -3.5 |
| Glycine | Gly | G | nonpolar | neutral | -0.4 |
| Histidine | His | H | polar | positive | -3.2 |
| Isoleucine | Ile | I | nonpolar | neutral | 4.5 |
| Leucine | Leu | L | nonpolar | neutral | 3.8 |
| Lysine | Lys | K | polar | positive | -3.9 |
| Methionine | Met | M | nonpolar | neutral | 1.9 |
| Phenylalanine | Phe | F | nonpolar | neutral | 2.8 |
| Proline | Pro | P | nonpolar | neutral | -1.6 |
| Serine | Ser | S | polar | neutral | -0.8 |
| Threonine | Thr | T | polar | neutral | -0.7 |
| Tryptophan | Trp | W | nonpolar | neutral | -0.9 |
| Tyrosine | Tyr | Y | polar | neutral | -1.3 |
| Valine | Val | V | nonpolar | neutral | 4.2 |

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent homology between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position; when a position in the first sequence is occupied by a similar nucleotide as the corresponding position in the second sequence, then the molecules are similar at that position. The percent homology between the two sequences is a function of the number of identical and similar positions shared by the sequences, taking into account the number of gaps, and the length of each gap, which needs to be introduced for optimal alignment of the two sequences. Representative algorithms and computer programs useful in determining the percent homology between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent homology between two nucleotide sequences can, alternatively, be determined for example using the GAP program in the GCG software package using an NWSgapdna.CMP matrix.

Human antibody: as used herein, is intended to include antibodies having variable and constant regions generated (or assembled) from human immunoglobulin sequences. In some embodiments, antibodies (or antibody components) may be considered to be "human" even though their amino acid sequences include residues or elements not encoded by human germline immunoglobulin sequences (e.g., include sequence variations, for example that may (originally) have been introduced by random or site-specific mutagenesis in vitro or by somatic mutation in vivo), for example in one or more CDRs and in particular CDR3.

Humanized: as is known in the art, the term "humanized" is commonly used to refer to antibodies (or antibody components) whose amino acid sequence includes $V_H$ and $V_L$ region sequences from a reference antibody raised in a non-human species (e.g., a mouse), but also includes modifications in those sequences relative to the reference antibody intended to render them more "human-like", i.e., more similar to human germline variable sequences. In some embodiments, a "humanized" antibody (or antibody component) is one that immunospecifically binds to an antigen of interest and that has a framework (FR) region having substantially the amino acid sequence as that of a human antibody, and a complementary determining region (CDR) having substantially the amino acid sequence as that of a non-human antibody. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor immunoglobulin) and all or substantially all of the framework regions are those of a human immunoglobulin consensus sequence. In some embodiments, a humanized antibody also comprises at least a portion of an immunoglobulin constant region (Fc), typically that of a human immunoglobulin constant region. In some embodiments, a humanized antibody contains both the light chain as well as at least the variable domain of a heavy chain. The antibody also may include a $C_H1$, hinge, $C_H2$, $C_H3$, and, optionally, a $C_H4$ region of a heavy chain constant region. In some embodiments, a humanized antibody only contains a humanized $V_L$ region. In some embodiments, a humanized antibody only contains a humanized $V_H$ region. In some certain embodiments, a humanized antibody contains humanized $V_H$ and $V_L$ regions.

Identity: As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 70%, 75%, 80%, 85%, 90%, 95%, or 99% identical. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgap-dna.CMP matrix.

$K_D$: as used herein, refers to the dissociation constant of a binding agent (e.g., an antibody or binding component thereof) from a complex with its partner (e.g., the epitope to which the antibody or binding component thereof binds).

Patient or subject: As used herein, the term "patient" or "subject" refers to any organism to which provided compound or compounds described herein are administered in accordance with the present disclosure e.g., for experimental, diagnostic, prophylactic, and/or therapeutic purposes. Typical subjects include animals (e.g., mammals such as mice, rats, rabbits, non-human primates, and humans). In one embodiment, the subject is human. In some embodiments, the subject may be suffering from, and/or susceptible to a disease, disorder, and/or condition (e.g., cancer). As used herein, a "patient population" or "population of subjects" refers to a plurality of patients or subjects.

Pharmaceutical composition: As used herein, the term "pharmaceutical composition" refers to a composition in which an active agent (e.g., a KIR3DL1 antibody agent) is formulated together with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces. In some embodiments, an active agent (e.g., a KIR3DL1 antibody agent) is formulated for parenteral administration.

Pharmaceutically acceptable: As used herein, the term "pharmaceutically acceptable" applied to the carrier, diluent, or excipient used to formulate a composition as disclosed herein means that the carrier, diluent, or excipient must be compatible with the other ingredients of the composition and not deleterious to the recipient thereof.

"Separate" administration as used herein refers to an administration of at least two active ingredients at the same time or at substantially the same time by different routes.

"Sequential" administration as used herein refers to administration of at least two active ingredients at different times, the administration route being identical or different. More particularly, sequential administration refers to the whole administration of one of the active ingredients before administration of the other or others commences. It is thus possible to administer one of the active ingredients over several minutes, hours, or days before administering the other active ingredient or ingredients. There is no simultaneous treatment in this case.

"Simultaneous" administration as used herein refers to the administration of at least two active ingredients by the same route and at the same time or at substantially the same time.

Specific binding: As used herein, the term "specific binding" refers to an ability to discriminate between possible binding partners in the environment in which binding is to occur. A binding agent that interacts with one particular target when other potential targets are present is said to "bind specifically" to the target with which it interacts. In some embodiments, specific binding is assessed by detecting or determining degree of association between the binding agent and its partner; in some embodiments, specific binding is assessed by detecting or determining degree of dissociation of a binding agent-partner complex; in some embodiments, specific binding is assessed by detecting or determining ability of the binding agent to compete an alternative interaction between its partner and another entity. In some embodiments, specific binding is assessed by performing such detections or determinations across a range of concentrations.

Therapeutically Effective Amount: As used herein, "therapeutically effective amount" means an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays progression of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

Treatment: As used herein, the term "treatment" (also "treat" or "treating") refers to any administration of a therapy that partially or completely alleviates, ameliorates, relieves, inhibits, delays progression of, reduces severity of, and/or reduces incidence of one or more symptoms, features, and/or causes of a particular disease, disorder, and/or condition. In some embodiments, such treatment may be of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, the subject is known to have one or more susceptibility factors that are statistically correlated with increased risk of development of the relevant disease, disorder, and/or condition.

Killer Immunoglobulin-Like Receptors

Natural Killer (NK) cells are lymphocytes with innate anti-viral and anti-tumor capacity. NK cells monitor cell surfaces of autologous cells for an aberrant expression of MHC class I molecules and cell stress markers. NK cells have been implicated in the immune defense against tumors.

NK cell potency is determined by the balance of various activating and inhibitory signals delivered through cell surface receptors. The most studied receptors known to modulate NK activity are the killer immunoglobulin-like receptors (KIR), whose interaction with HLA class I ligands are important for NK function (Parham, P., *Nat Rev Immunol*, 2005. 5(3): p. 201-14; Kim, S., et al., *Nature*, 2005. 436 (7051): p. 709-13).

Human killer-cell Ig-like receptors (KIRs) are a large family of receptors present on certain subsets of lymphocytes, including NK cells. KIRs are glycoproteins that are expressed on surfaces of NK cells and bind to major histocompatibility complex (MHC)/human leukocyte antigen (HLA) class I subtypes on potential target cells. This binding interaction is believed to inhibit the cytotoxicity of NK cells. One approach to treat cancer is by removing inhibition of immune response directed by NK cells. Monoclonal antibodies that target KIRs have been shown in clinical trials to block such inhibition, relieving the suppression of NK activity. (Romagne et al, 2009, *Blood* 114:2667-2677).

Three criteria have been used to categorize KIRs into at least 13 groups: 1) the number of extracellular Ig-like domains (domains D0, D1, D2), 2) cytoplasmic tail length (long or short), and 3) sequence analogy. The 13 groups of KIRs include KIR3DL1-2, KIR3DS1, KIR2DL1-5, and KIR2DS1-5. The nomenclature for KIRs is based upon the number of extracellular domains (e.g., KIRs with 2 or 3 extracellular domains are referred to as KIR2D or KIR3D, respectively) and whether the cytoplasmic tail is either long (e.g., KIR3DL) or short (e.g., KIR3DS).

Within humans, the presence or absence of a given KIR is variable from one NK cell to another within the NK population present in a single individual. Moreover, within the human population there is a relatively high level of polymorphism of the KIR molecules, with certain KIR molecules being present in some, but not all individuals. Certain KIR gene products function as activating receptors that stimulate lymphocyte activity following engagement with the appropriate ligand. Certain KIR gene products function as inhibitory receptors. In general, the known inhibitory KIR receptors possess long (L) cytoplasmic tails and include members of the KIR2DL and KIR3DL subfamilies. The present disclosure provides, at least in part, antibody agents that bind to inhibitory KIR receptors and in particular, antibody agents that bind to KIR3DL molecules (also known as CD158e). In some embodiments, the antibody agents that binds to KIR3DL1 is an antibody or an antigen binding fragment thereof.

Each of the KIR genes exhibits allelic variation. The polymorphisms between the alleles of a given KIR gene can occur in its extracellular, transmembrane, or cytoplasmic domains. Polymorphism at each of these 3 domains has significant biologic consequences. The KIR3DL1/Si gene locus, ubiquitous in human populations, is one of the most polymorphic of the KIR genes, and the only locus whose alleles encode for both inhibitory (KIR3DL1) and activating (KIR3DS1) receptors (Parham, P., et al., *J. Immunol.*, 2011. 187: p. 11-19; Vivian, F., et al., *Nature*, 2011. 479: p. 401-406; Halfpenny, I., et al., *Hum. Immunol.*, 2004. 65: p. 602-612; Gardiner, C., et al., *J. Immunol.*, 2001. 166: p. 2992-3001; Gumperz, J. E., et al., *J. Exp. Med.*, 1996. 183: p. 1817-1827). KIR3DL1 subtypes are displayed at high or low cell surface densities (KIR3DL1-h or KIR3DL1-1, respectively) or retained within the cell (KIR3DL1-n). KIR3DS1 receptors are displayed on the cell surface, but not known to bind HLA-Bw4 (Carr, W., M. Pando, and P. Parham, *J. Immunol.*, 2005. 175: p. 5222-5229; Gillespie, G., et al., *AIDS Res. Hum. Retroviruses*, 2007. 23: p. 451-455). Dimorphism between isoleucine and threonine at position 80 in HLA-Bw4 (Bw4-80I vs Bw4-80T) may similarly impact the density of its surface expression on healthy cells and influence the strength of binding to KIR3DL1 subtypes (Saunders, P., et al., *J. Exp. Med.*, 2016. 213 p. 791-807).

The present disclosure encompasses the recognition that modulating the activity of particular KIR3DL subtypes may have clinical benefits. In some embodiments, it is envisioned that inhibition of KIR3DL1 and/or particular KIR3DL1 alleles may be clinically relevant in patients with cancer, such as acute myelogenous leukemia (AML) or neuroblastoma. In some embodiments, patients with certain KIR3DL1 alleles and/or ligands may be predisposed or susceptible to acute myelogenous leukemia (AML) and/or in patients with neuroblastoma. For example, among NK cell receptor-ligand partnerships, KIR3DL1 and HLA-Bw4 demonstrate the greatest diversity (Boudreau, J., et. al., *PLoS ONE*, 2014. 9: p. e99543). Moreover, allelic combinations of KIR3DL1-h and Bw4-80I, a strongly-binding receptor-ligand combination, are enriched among patients with AML, suggesting that this genetic combination may predispose individuals to developing cancer (Shen, M., Y. Linn, and E. Ren, *Immunogenetics*, 2016. 68: p. 133-144). Moreover, in patients with AML receiving a bone marrow transplant, relapse is less likely if the donor has KIR3DL1 alleles that are weakly inhibited or not inhibited by HLA-Bw4 in the patient, in comparison to patients whose donors have KIR3DL1 alleles that are highly inhibited (unpublished data). Patients who lack the HLA-Bw4 ligand have similarly good outcomes. In neuroblastoma patients treated with anti-GD2 antibody, KIR3DL1 and HLA-B subtype combinations with weak or no engagement of KIR3DL1 are similarly associated with superior tumor control and more favorable disease-free survival compared to combinations with strong interaction (Forlenza, C., et al., *J. Clin. Oncol.*, 2016. 34: p. 2443-2451). Without wishing to be bound by theory, these data suggest that strong inhibition through KIR3DL1 may lead to worse outcomes in AML and NB patients. In some embodiments, an inhibitory antibody agent that binds to KIR3DL1 may be clinically beneficially for treating cancer. In some embodiments, an anti-KIR3DL1 antibody agent that blocks the inhibitory interaction between KIR3DL1 and its ligand HLA-Bw4 may enhance NK response in cancer patients, such as AML and NB patients.

KIR Antibody Agents

The present disclosure provides, at least in part, KIR antibody agents (e.g., KIR3DL1 antibody agents) and methods of making and using the same. For example, the disclosure provides antibody agents that target KIR3DL1. In some embodiments, the KIR antibody agent (e.g., a KIR3DL1 antibody agent) is capable of activating NK cells. In some embodiments, the KIR antibody agent (e.g., a KIR3DL1 antibody agent) is capable of enhancing NK killing of target cancer cells. In some embodiments, the KIR antibody agent (e.g., a KIR3DL1 antibody agent) enhances ADCC activity (e.g., ADCC activity mediated by NK cells).

The present disclosure encompasses a recognition that, in at least in certain patients, it may be beneficial to target particular subtypes and alleles of KIRs. In some embodiments, the disclosure provides antibody agents that target one or more subtypes of KIR3DL1. In some embodiments, a KIR3DL1 antibody agent of the present technology binds one or more allele subtypes such as 005-group low (*005), 007-group low (*007), 001-group high (*001, *016), 002-group high (*002, *008, *009, *015, *020), activating KIR3DS1 (*013) and/or null subtype. In some embodiments, the KIR3DL1 antibody agent binds to a KIR3DL1 allele, such as *001, *016, *026, *027, *043, *052, *059, *060, *061, *064, *065, *067, *075, *002, *015, *008, *009, *020, *006, *017, *018, *022, *023, *024N, *025, *028, *029, *030, *031, *034, *035, *038, *042, *051, *054, *057, *062, *067, *074, *076, *077, *005, *041, *044, *053, *007, *032, *030, *068, *013, *010, *011, *012, *014, *045, *046, *047, *048, *049N, *050, *055, *058, *073, *004, *019, *021, *036, *037, *039, *040, *056, *063, and/or *072.

In some embodiments, the present disclosure provides anti-KIR3DL1 antibody agents that have variable affinity for different KIR3DL1 alleles. In some embodiments, a KIR3DL1 antibody agent of the present technology binds specifically to one, two, three, four, five or more alleles of KIR3DL1. In some embodiments, the KIR3DL1 antibody agent binds to an epitope within the extracellular domain of KIR3DL1. In some embodiments, the KIR3DL1 antibody agent specifically binds to one, two, three, four, five, six, seven, eight, nine, ten or more alleles of KIR3DL1, such as *001, *016, *026, *027, *043, *052, *059, *060, *061, *064, *065, *067, *075, *002, *015, *008, *009, *020, *006, *017, *018, *022, *023, *024N, *025, *028, *029, *030, *031, *034, *035, *038, *042, *051, *054, *057, *062, *067, *074, *076, *077, *005, *041, *044, *053, *007, *032, *030, *068, *013, *010, *011, *012, *014, *045, *046, *047, *048, *049N, *050, *055, *058, *073, *004, *019, *021, *036, *037, *039, *040, *056, *063, and/or *072.

In some embodiments, the KIR3DL1 antibody agent specifically binds to an epitope within the extracellular domain of one or more alleles of KIR3DL1. In some embodiments, the KIR3DL1 antibody agent specifically binds to an epitope within the extracellular domain of one, two, three, four, five, six, seven, eight, nine, ten or more of *001, *016, *026, *027, *043, *052, *059, *060, *061, *064, *065, *067, *075, *002, *015, *008, *009, *020, *006, *017, *018, *022, *023, *024N, *025, *028, *029, *030, *031, *034, *035, *038, *042, *051, *054, *057, *062, *067, *074, *076, *077, *005, *041, *044, *053, *007, *032, *030, *068, *013, *010, *011, *012, *014, *045, *046, *047, *048, *049N, *050, *055, *058, and/or *073. For example, in some embodiments, the KIR3DL1 antibody agent specifically binds to an epitope within the extracellular domain of one or more of *001, *002, *007/015, *020, and *033. In some embodiments, the KIR3DL1 antibody agent specifically binds to an epitope within the extracellular domain of two or more alleles of KIR3DL1 selected from *001, *002, *007/015, *020, and *033.

In some embodiments, KIR antibody agents of the present disclosure exhibit high affinity binding for one or more alleles of the target antigen (e.g., a KIR3DL1 receptor). In some embodiments, KIR antibody agents of the present disclosure exhibit high affinity binding for an epitope within the extracellular domain of one or more alleles of the target antigen (e.g., a KIR3DL1 receptor). In some embodiments, binding of the KIR antibody agent to a KIR (e.g., a KIR3DL1) blocks binding of one or more cognate HLA molecules (e.g., HLA-Bw4).

In some embodiments, a KIR antibody agent of the present disclosure binds to a KIR (e.g., a KIR3DL1) with a $K_D$ in the range of 0.01 nM to 100 nM. In some embodiments, the KIR antibody agent binds to a KIR with a $K_D$ of about 1 nM to 50 nM. In some embodiments, the KIR antibody agent bind to KIR3DL1. In some embodiments, the KIR3DL1 antibody agent binds to one or more KIR3DL1 alleles with a $K_D$ in the range of 0.01 nM to 100 nM. In some embodiments, the KIR3DL1 antibody agent binds to one or more KIR3DL1 alleles with a $K_D$ in the range of 1 nM to 50 nM. In some embodiments, the KIR3DL1 antibody agent binds to one or more KIR3DL1 alleles with a $K_D$ in the range of 4 nM to 30 nM.

In some embodiments, the KIR antibody agent binds specifically to one or more KIR alleles. In some embodiments, the KIR3DL1 antibody agent binds specifically to one or more KIR3DL1 alleles. In some embodiments, the KIR3DL1 antibody agent binds to one or more alleles of KIR3DL1 with high affinity, wherein the one or more alleles is selected from *001, *016, *026, *027, *043, *052, *059, *060, *061, *064, *065, *067, *075, *002, *015, *008, *009, *020, *006, *017, *018, *022, *023, *024N, *025, *028, *029, *030, *031, *034, *035, *038, *042, *051, *054, *057, *062, *067, *074, *076, *077, *005, *041, *044, *053, *007, *032, *030, *068, *013, *010, *011, *012, *014, *045, *046, *047, *048, *049N, *050, *055, *058, *073, *004, *019, *021, *036, *037, *039, *040, *056, *063, and *072. In some embodiments, the KIR3DL1 antibody agent binds to one or more alleles of KIR3DL1 with a $K_D$ in the range of 0.01 nM to 100 nM. In some embodiments, the KIR3DL1 antibody agent binds to one or more alleles of KIR3DL1 with a $K_D$ in the range of about 1 nM to 50 nM. In some embodiments, the KIR3DL1 antibody agent binds to an epitope on the extracellular domain of one or more KIR3DL1 alleles with a $K_D$ in the range of 0.001 nM to 100 nM, or 0.1 nM to 100 nM, or 1 nM to 50 nM, or 0.1 nM to 30 nM, or 3 nM to 30 nM, wherein the one or more alleles is selected from *001, *016, *026, *027, *043, *052, *059, *060, *061, *064, *065, *067, *075, *002, *015, *008, *009, *020, *006, *017, *018, *022, *023, *024N, *025, *028, *029, *030, *031, *034, *035, *038, *042, *051, *054, *057, *062, *067, *074, *076, *077, *005, *041, *044, *053, *007, *032, *030, *068, *013, *010, *011, *012, *014, *045, *046, *047, *048, *049N, *050, *055, *058, *073, *004, *019, *021, *036, *037, *039, *040, *056, *063, and *072. In some embodiments, the $K_D$ is within a range of about 1 nM to 50 nM. In some embodiments, the KIR3DL1 antibody agent binds to an epitope on the extracellular domain of one or more KIR3DL1 alleles with a $K_D$ in the range of about 1 nM to 50 nM, wherein one or more KIR3DL1 alleles include *001, *002, *007, *015, *020, and/or *033.

In some embodiments, it may be desirable to alter the affinity of a human or humanized KIR antibody agent for its target KIR (e.g., KIR3DL1). In some embodiments, it may be desirable to increase the affinity of a human or humanized KIR antibody agent for its target KIR (e.g., KIR3DL1). In some embodiments, the KIR antibody agent is capable of blocking the interaction between an inhibitory KIR with its HLA ligand. In some embodiments the HLA ligand is HLA-Bw4. In some embodiments, the KIR antibody agent is capable of preventing or reducing KIR3DL1-mediated inhibition of NK cell activation.

In some embodiments, the KIR antibody agent is capable of activating NK cells. In some embodiments, the KIR antibody agent is capable of enhancing NK killing of target cancer cells. In some embodiments, target cancer cells can include leukemia cells (e.g., AML). In some embodiments, the KIR antibody agent can enhance ADCC activity by blocking or reducing the interaction between KIR3DL1 and HLA-Bw4.

Those of ordinary skill in the art will appreciate that KIR antibody agents as described herein may be provided and/or utilized in any of a variety of formats. In general, as described herein, KIR3DL1 antibody agents can be or include, e.g., a polyclonal antibody; a monoclonal antibody or antigen binding fragment thereof; a modified antibody such as a chimeric antibody, reshaped antibody, humanized antibody, or antigen binding fragment thereof (e.g., Fab', Fab, F(ab')$_2$); or a biosynthetic antibody, e.g., a single chain antibody, single domain antibody (DAB), Fv, single chain Fv (scFv), or a zybody, or the like.

KIR antibody agents (e.g., antibody agents that bind to KIR3DL1) can be generated using methods known in the art. For example, protocols for antibody production are described by Harlow and Lane, Antibodies: A Laboratory Manual, (1988). In some embodiments, monoclonal antibodies may be generated using phage display. To ensure the recovery of high affinity, monoclonal antibodies, a combinatorial immunoglobulin library typically contains a large repertoire size. A typical strategy utilizes mRNA obtained from lymphocytes or spleen cells of immunized mice to synthesize cDNA using reverse transcriptase. The heavy and light chain genes are amplified separately by PCR and ligated into phage cloning vectors. Two different libraries are produced, one containing the heavy chain genes and one containing the light chain genes. Phage DNA is isolated from each library, and the heavy and light chain sequences are ligated together and packaged to form a combinatorial library. Each phage contains a random pair of heavy and light chain cDNAs and upon infection of *E. coli* directs the expression of the antibody chains in infected cells. To identify an antibody that recognizes the antigen of interest, the phage library is plated, and the antibody molecules present in the plaques are transferred to filters. The filters are incubated with radioactively labeled antigen and then washed to remove excess unbound ligand. A radioactive spot on the autoradiogram identifies a plaque that contains an antibody that binds the antigen. Cloning and expression vectors that are useful for producing a human immunoglobulin phage library can be obtained, for example, from Stratagene Cloning Systems (La Jolla, Calif.).

A similar strategy can be employed to obtain high-affinity scFv (see, e.g., Vaughn et al., 1996, *Nat. Biotechnol.*, 14:309-314). An scFv library with a large repertoire can be constructed by isolating V-genes from non-immunized human donors using PCR primers corresponding to all known V$_H$, Vκ and Vλ gene families. Following amplification, the Vκ and Vλ pools are combined to form one pool. These fragments are ligated into a phagemid vector. An scFv linker (e.g., [G$_4$S]$_3$ (SEQ ID NO: 64)) is then ligated into the phagemid upstream of the V$_L$ fragment. The V$_H$ and linker-V$_L$ fragments are amplified and assembled on the J$_H$ region. The resulting V$_H$-linker-V$_L$ fragments are ligated into a phagemid vector. The phagemid library can be panned using filters, as described above, or using immunotubes (Nunc; Maxisorp). Similar results can be achieved by constructing a combinatorial immunoglobulin library from lymphocytes or spleen cells of immunized rabbits and by expressing the scFv constructs in *P. pastoris* (see, e.g., Ridder et al., 1995, *Biotechnology*, 13:255-260). Additionally, following isolation of an appropriate scFv, antibody fragments with higher binding affinities and slower dissociation rates can be obtained through affinity maturation processes such as CDR3 mutagenesis and chain-shuffling (see, e.g., Jackson et al., 1998, *Br. J. Cancer,* 78:181-188); Osbourn et al., 1996, *Immunotechnology*, 2:181-196).

In some embodiments, the KIR antibody agent (e.g., a KIR3DL1 antibody agent) is a human monoclonal antibody or an antigen binding fragment thereof. Human antibodies can be produced using various techniques, including phage display libraries (Hoogenboom et al., 1991, *Mol. Immunol.* 28(9): 1027-37; Marks et al., 1991, *J. Mol. Biol.* 222(3): 581-97) and the preparation of human monoclonal antibodies (Reisfeld and Sell, 1985, *Cancer Surv.* 4(1):271-90). Similarly, introducing human Ig genes into transgenic animals in which the endogenous Ig genes have been partially or completely inactivated can be exploited to synthesize human antibodies (see, e.g., Fishwild et al., 1996, *Nat. Biotechnol.* 14(7):845-51; Lonberg et al., 1994, *Nature* 368(6474):856-9; Lonberg and Huszar, 1995, *Int. Rev. Immunol.* 13:65-93; Taylor, L. D., et al., 1992, *Nucl. Acids Res.* 20:6287-6295; Kellermann S-A., and Green L. L., 2002, *Curr. Opin. Biotechnol.* 13:593-597; Little, M. et al., 2000, *Immunol. Today* 21:364-370; Murphy, A. J. et al., 2014, *Proc. Natl. Acad. Sci. U.S.A.* 111(14):5153-5158). Upon challenge, human antibody production is observed. In some embodiments, KIR3DL1 human antibodies are made by immunization of non-human animals engineered to make human antibodies.

In some embodiments, the KIR antibody agent (e.g., a KIR3DL1 antibody agent) is a humanized antibody or a fragment thereof. Humanized forms of non-human antibodies are chimeric immunoglobulins (Igs), Ig chains or antigen binding fragments (such as Fv, Fab, Fab', F(ab')$_2$ or other antigen-binding subsequences of antibodies) that contain minimal sequence derived from non-human Ig. Generally, a humanized antibody has one or more amino acid residues introduced from a non-human source. These non-human amino acid residues are often referred to as "import" residues, which are typically taken from an "import" variable domain. Humanization is accomplished by substituting animal (e.g., rodent) complementarity determining regions (CDRs) or CDR sequences for the corresponding sequences of a human antibody (Riechmann et al., 1988, *Nature* 332(6162):323-7; Verhoeyen et al., 1988, *Science* 239 (4847): 1534-6). Such "humanized" antibodies are chimeric antibodies (see, e.g., U.S. Pat. Nos. 4,816,567; 5,693,762; and 5,225,539), wherein substantially less than an intact human variable domain has been substituted by the corresponding sequence from a non-human species. In some embodiments, humanized antibodies are typically human antibodies in which some CDR residues and possibly some framework (FR) residues are substituted by residues from analogous sites in rodent Abs. Humanized antibodies include human Igs (recipient antibody) in which residues from a CDR of the recipient are replaced by residues from a CDR of a non-human species (donor antibody) such as mouse, rat or rabbit, having the desired specificity, affinity and capacity. In some instances, corresponding non-human residues replace Fv framework residues of the human Ig. Humanized antibodies may comprise residues that are found neither in the recipient antibody nor in the imported CDR or framework sequences. In general, the humanized antibody comprises substantially all of at least one, and typically two, variable domains, in which most if not all of the CDR regions correspond to those of a non-human Ig and most if not all of the FR regions are those of a human Ig consensus sequence. The humanized antibody optimally also comprises at least a portion of an Ig constant region (Fc), typically that of a human Ig (Riechmann et al., 1988, *Nature* 332(6162):323-7; Verhoeyen et al., 1988, *Science* 239 (4847): 1534-6).

In some embodiments, a provided antibody agent is or comprises an antibody that is a member of an antibody class selected from the group consisting of IgG, IgM, IgA, IgD, IgE, or an antigen binding fragment thereof. In some embodiments, the KIR3DL1 antibody agent is or comprises an IgG1, IgG2, IgG3, IgG4 domain. In some embodiments, a KIR3DL1 antibody agent is or comprises an IgG1 domain. In some embodiments, a KIR3DL1 antibody agent is or comprises a monoclonal antibody (e.g., human monoclonal antibody) or an antigen binding fragment thereof. In some embodiments, the KIR3DL1 antibody agent is or comprises a monoclonal IgG1 antibody (e.g., human monoclonal IgG1 antibody) or an antigen binding fragment thereof. In some embodiments, the antigen binding fragment of a KIR3DL1 monoclonal antibody (e.g., human KIR3DL1 monoclonal antibody) is an scFv.

In some embodiments, the KIR3DL1 antibody agent is a monoclonal antibody that comprises a variant Fc region, wherein said variant Fc region comprises at least one amino acid modification relative to a wild-type Fc region (or the parental Fc region). In some embodiments, a variant Fc region has an altered affinity for an Fc receptor (e.g., an FcγR), provided that said variant Fc region does not have a substitution at positions that make a direct contact with Fc receptor based on crystallographic and structural analysis of Fc-Fc receptor interactions such as those disclosed by Sondermann et al., 2000, *Nature,* 406:267-273. Examples of positions within the Fc region that make a direct contact with an Fc receptor such as an FcγR are amino acids 234-239 (hinge region), amino acids 265-269 (B/C loop), amino acids 297-299 (C'/E loop), and amino acids 327-332 (F/G) loop. In some embodiments, the KIR3DL1 monoclonal antibody is a human KIR3DL1 monoclonal antibody comprising a variant Fc region which has a modification of at least one residue that makes a direct contact with an FcγR.

In some embodiments, the present disclosure provides and/or utilizes antibodies or antibody agents comprising a variant Fc region (i.e., an Fc region includes one or more additions, deletions, and/or substitutions relative to an appropriate reference Fc) that are characterized in that effector function is altered relative to a reference Fc, and/or affinity for an FcR is enhanced or diminished relative to a reference Fc. These variations are within the skill of a person in the art.

It will be appreciated that KIR3DL1 antibody agents may be engineered, produced, and/or purified in such a way as to improve characteristics and/or activity of the antibody agents. For example, improved characteristics of provided antibody agents include, but are not limited to, increased stability, improved binding affinity and/or avidity, increased binding specificity, increased production, decreased aggregation, decreased nonspecific binding, among others.

The identification of one or more antibodies that bind(s) to substantially or essentially the same epitope as the anti-KIR3DL1 antibody agents described herein can be readily determined using any one of variety of immunological screening assays in which antibody competition can be assessed. A number of such assays are routinely practiced and well known in the art (see, e.g., U.S. Pat. No. 5,660, 827). It will be understood that actually determining the epitope to which an antibody agent described herein binds, is not in any way required to identify an antibody that binds to the same or substantially the same epitope as the antibody agent described herein.

For example, where the test antibodies to be examined are obtained from different source animals, or are even of a different Ig isotype, a simple competition assay may be employed in which the control and test antibodies are admixed (or pre-adsorbed) and applied to a sample containing KIR3DL polypeptides. Protocols based upon Western blotting and the use of BIACORE analysis are suitable for use in such simple competition studies.

In one embodiments, one pre-mixes the control antibodies with varying amounts of the test antibodies (e.g., about 1:10 or about 1:100) for a period of time prior to applying to the KIR3DL1 antigen sample. In other embodiments, the control and varying amounts of test antibodies can simply be admixed during exposure to the KIR3DL1 antigen sample. As long as one can distinguish bound from free antibodies (e.g., by using separation or washing techniques to eliminate unbound antibodies) and control KIR3DL1 antibodies from the test antibodies (e.g., by using species-specific or isotype-specific secondary antibodies or by specific labeling with a detectable label), one can determine if the test antibodies reduce the binding of control KIR3DL1 antibodies to the antigens, indicating that the test antibody recognizes substantially the same epitope as the control KIR3DL1 antibody. The binding of the (labeled) control KIR3DL1 antibodies in the absence of a completely irrelevant antibody can serve as the control high value. The control low value can be obtained by incubating the labeled control KIR3DL1 antibodies with unlabelled antibodies of exactly the same type, where competition would occur and reduce binding of the labeled antibodies. In a test assay, a significant reduction in labeled antibody reactivity in the presence of a test antibody is indicative of a test antibody that recognizes substantially the same epitope. Any test antibody that reduces the binding of control antibody to KIR3DL1 antigens by at least about 50%, such as at least about 60%, or at least about 70% (e.g., about 65-100%), at any ratio of control:test antibody between about 1:10 and about 1:100 is considered to be an antibody that binds to substantially the same epitope or determinant as control KIR3DL1 antibody.

Competition can be assessed by, for example, a flow cytometry test. In such a test, cells bearing a KIR3DL1 polypeptide can be incubated first with control KIR3DL1 antibody, for example, and then with the test antibody labeled with a fluorochrome or biotin. The antibody is said to compete with control KIR3DL1 antibody if the binding obtained upon preincubation with a saturating amount of control KIR3DL1 antibody is about 80%, about 50%, about 40% or less (e.g., about 30%) of the binding (as measured by mean of fluorescence) obtained by the antibody without preincubation with control KIR3DL1 antibody. Alternatively, an antibody is said to compete with control KIR3DL1 antibody if the binding obtained with a labeled control KIR3DL1 antibody (by a fluorochrome or biotin) on cells preincubated with a saturating amount of test antibody is about 80%, about 50%, about 40%, or less (e.g., about 30%) of the binding obtained without preincubation with the test antibody.

A simple competition assay in which a test antibody is pre-adsorbed and applied at saturating concentration to a surface onto which a KIR3DL1 antigen is immobilized may also be employed. The surface in the simple competition assay may be a BIACORE chip (or other media suitable for surface plasmon resonance analysis). The control antibody is then brought into contact with the surface at a KIR3DL1-saturating concentration and the KIR3DL1 and surface binding of the control antibody is measured. This binding of the control antibody is compared with the binding of the control antibody to the KIR3DL1-containing surface in the absence of test antibody. In a test assay, a significant reduction in binding of the KIR3DL1-containing surface by the control antibody in the presence of a test antibody relative to that observed in the absence of the test antibody indicates that the test antibody recognizes substantially the same epitope as the control antibody. Any test antibody that reduces the binding of control antibody to a KIR3DL1 antigen by at least about 30% or more, such as about 40%, can be considered to be an antibody that binds to substantially the same epitope or determinant as a control. In certain embodiments, such a test antibody will reduce the binding of the control antibody to the KIR3DL1 antigen by at least about 50% (e.g., at least about 60%, at least about 70%, or more). It will be appreciated that the order of control and test antibodies can be reversed: that is, the control antibody can be first bound to the surface and the test antibody is brought into contact with the surface thereafter in a competition assay. In some embodiments, the antibody having higher affinity for the KIR3DL1 antigen is bound to the surface first, as it will be expected that the decrease in binding seen for the second antibody (assuming the antibodies are cross-reacting) will be of greater magnitude. Further examples of such assays are provided in, e.g., Saunal (1995) *J. Immunol. Methods* 183: 33-41, the disclosure of which is incorporated herein by reference.

Determination of whether an antibody binds within one of the epitope regions defined above can be carried out in ways known to the person skilled in the art. As one example of such mapping/characterization methods, an epitope region for an anti-KIR3DL1 antibody may be determined by epitope "foot-printing" using chemical modification of the exposed amines/carboxyls in the KIR3DL1 protein. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. See, e.g., Ehring H, *Analytical Biochemistry*, Vol. 267 (2) pp. 252-259 (1999) Engen, J. R. and Smith, D. L. (2001) *Anal. Chem.* 73, 256A-265A. Another example of a suitable epitope identification technique is nuclear magnetic resonance epitope mapping (NMR), where typically the position of the signals in two-dimensional NMR spectra of the free antigen and the antigen complexed with the antigen binding peptide, such as an antibody, are compared. The antigen typically is selectively isotopically labeled with 15N so that only signals corresponding to the antigen and no signals from the antigen binding peptide are seen in the NMR-spectrum. Antigen signals originating from amino acids involved in the interaction with the antigen binding peptide typically will shift position in the spectrum of the complex compared to the spectrum of the free antigen, and the amino acids involved in the binding can be identified that way. See, e.g., Ernst, *Schering Res Found Workshop.* 2004; (44): 149-67; Huang et al. *Journal of Molecular Biology*, Vol. 281 (1) pp. 61-67 (1998); and Saito and Patterson, *Methods.* 1996 June; 9 (3): 516-24.

Epitope mapping/characterization also can be performed using mass spectrometry methods. See, e.g., Downward, *J Mass Spectrom.* 2000 April; 35 (4): 493-503 and Kiselar and Downard, *Anal Chem.* 1999 May 1; 71 (9): 1792-801. Protease digestion techniques also can be useful in the context of epitope mapping and identification. Antigenic determinant-relevant regions/sequences can be determined by protease digestion, e.g., by using trypsin in a ratio of about 1:50 to KIR3DL1 or overnight digestion at and pH 7-8, followed by mass spectrometry (MS) analysis for peptide identification. The peptides protected from trypsin cleavage by the anti-KIR3DL1 binder can subsequently be identified by comparison of samples subjected to trypsin digestion and samples incubated with antibody and then subjected to digestion by e.g., trypsin (thereby revealing a footprint for the binder). Other enzymes like chymotrypsin, pepsin, etc., also or alternatively can be used in similar epitope characterization methods. Moreover, enzymatic digestion can provide a quick method for analyzing whether a potential antigenic determinant sequence is within a region of the KIR3DL1 polypeptide that is not surface exposed and, accordingly, most likely not relevant in terms of immunogenicity/antigenicity.

Specific Exemplary Embodiments

In some embodiments, the present disclosure provides KIR3DL1 antibody agents comprising a heavy chain variable region, wherein the heavy chain variable region comprises a CDR1 with a sequence set forth as SEQ ID NO:62 and a CDR2 with a sequence set forth as SEQ ID NO: 63.

SEQ ID NO: 62—$GX_1X_2FX_3X_4YX_5$, wherein $X_1$ is Y or F or G, $X_2$ is T or S, $X_3$ is T or S or D or G, $X_4$ is G or S or D, and $X_5$ is Y or W or A or G.

SEQ ID NO: 63—$X_1X_2X_3X_4X_5X_6X_7X_8$, wherein $X_1$ is I or M, $X_2$ is N or S or Y, $X_3$ is P or W or S, $X_4$ is N or G or S, $X_5$ is S or D or G, $X_6$ is G or S, $X_7$ is G or Y or D or S or N, and Xg is T or I.

In some embodiments, the KIR3DL1 antibody agent comprises heavy and light chain variable regions, wherein the heavy chain variable region contains at least one of the CDRs found in a heavy chain variable region that appears in Table 1 and/or at least one of the CDRs found in a light chain variable region that appears in Table 1. In some embodiments, the KIR3DL1 antibody agent comprises a heavy chain variable region that contains at least two of the CDRs found in a heavy chain variable region that appears in Table 1 and/or has a light chain variable region that contains at least two of the CDRs found in a light chain variable region that appears in Table 1. In some embodiments, the KIR3DL1 antibody agent comprises a heavy chain variable region that contains three CDRs found in a heavy chain variable region that appears in Table 1 and/or has a light chain variable region that contains three of the CDRs found in a light chain variable region that appears in Table 1. In some embodiments, the KIR3DL1 antibody agent is a monoclonal antibody. In some embodiments, the KIR3DL1 antibody agent comprises heavy and light chain variable regions, wherein the heavy and/or light chain variable region contains three CDRs, in which each CDR has a sequence that is at least about 50% (e.g., at least about 55%, 60%, 65%, 70%, 75%, 80%, 85%, 90%, 95%, 96%, 97%, 98%, or 99%) identical to the CDRs that appear in Table 1. In some embodiments, the KIR3DL1 antibody agent comprises heavy and light chain variable regions, wherein the heavy and/or light chain variable region contains three CDRs, wherein the sequence of each of the CDRs comprises a sequence as listed in Table 1 or a sequence with 1, 2, 3, 4, or 5 amino acid substitutions.

TABLE 1

CDR sequences of exemplary KIR3DL1 antibodies

| Antibody | CDR1 | SEQ ID NO | CDR2 | SEQ ID NO | CDR3 | SEQ ID NO |
|---|---|---|---|---|---|---|
| 42 Lv | SSDVGGYNY | 20 | DVS | 21 | SSYTSSNTLV | 22 |
| 42 Hv | GYTFTGYY | 23 | INPNSGGT | 24 | ADLFY | 25 |
| 61 Lv | GGSLASKY | 26 | DDN | 27 | QSYDNSSVV | 28 |
| 61 Hv | GFTFDDYA | 29 | ISWNSGSI | 30 | ASSLRYFEWPIDY | 31 |
| 72 Lv | RSNIGNNA | 32 | YDD | 33 | AAWDDSLNG | 34 |
| 72 Hv | GFTFGDYG | 35 | INWNGGGT | 36 | ARVWGCGSTTCYEGADDAFDI | 37 |
| 73 Lv | QSLVHSDGNTY | 38 | GVS | 39 | MQGTHWPLT | 40 |
| 73 Hv | GYSFTSYW | 41 | IYPGDSDT | 42 | ARGREQLWLDGMDV | 43 |
| 74 Lv | SSNVGNNY | 44 | DNN | 45 | GTWDNSLRVEL | 46 |
| 74 Hv | GGTFSSYA | 47 | MNPNSGNT | 48 | ARYSFHLDG | 49 |
| 77 Lv | NIESKS | 50 | DDT | 51 | QVWDNRRDHVV | 52 |
| 77 Hv | GFTFSDYY | 53 | ISSSSSYT | 54 | AREGIAAADAFDI | 55 |
| 80 Lv | TGAVTSGHY | 56 | ETS | 57 | FLSYSGTVV | 58 |
| 80 Hv | GYTFTGYY | 59 | INPNSGGT | 60 | ARYGD | 61 |

In some embodiments, the KIR3DL1 antibody agent comprises a heavy chain variable region, wherein the heavy chain variable region comprises any one of SEQ ID NO: 7, 9, 11, 13, 15, 17, and 19. In some embodiments, the heavy chain variable region has a sequence that is at least about 70% (e.g., at least about 70%, 75%, 80%, 85%, 90%, 95%, 96%, 97%, 98%, or 99%) identical to any one of SEQ ID NO: 7, 9, 11, 13, 15, 17, and 19.

In some embodiments, the KIR3DL1 antibody agent comprises a light chain variable region, wherein the light chain variable region comprises any one of SEQ ID NO: 6, 8, 10, 12, 14, 16, and 18. In some embodiments, the light chain variable region has a sequence that is at least about 70% (e.g., at least about 70%, 75%, 80%, 85%, 90%, 95%, 96%, 97%, 98%, or 99%) identical to any one of SEQ ID NO: 6, 8, 10, 12, 14, 16, and 18.

In some embodiments, the KIR3DL1 antibody agent is comprises a heavy chain variable region and a light chain variable region wherein the heavy chain variable region has a sequence that is at least about 70% (e.g., at least about 70%, 75%, 80%, 85%, 90%, 95%, 96%, 97%, 98%, or 99%) identical to any one of SEQ ID NO: 7, 9, 11, 13, 15, 17, and 19 and wherein the light chain variable region has a sequence that is at least about 70% (e.g., at least about 70%, 75%, 80%, 85%, 90%, 95%, 96%, 97%, 98%, or 99%) identical to any one of SEQ ID NO: 6, 8, 10, 12, 14, 16, and 18. In some embodiments, the KIR3DL1 antibody agent comprises a heavy chain variable region and a light chain variable region, wherein the heavy chain variable region comprises any one of SEQ ID NO: 7, 9, 11, 13, 15, 17, and 19 and the light chain variable region comprises any one of SEQ ID NO: 6, 8, 10, 12, 14, 16, and 18.

Those skilled in the art, reading the present disclosure, will appreciate that provided antibody sequences, or antigen binding fragments thereof, may usefully be incorporated into any of a variety of immunoglobulin-based or other polypeptide formats; embodiments of the disclosure therefore include a variety of polypeptides and polypeptide formats including sequence elements, or antigen binding fragments thereof, as described herein. Included within such provided polypeptides and polypeptide formats are those that bind specifically to a KIR (e.g., KIR3DL1). In some embodiments, are provided polypeptides and polypeptide formats that bind specifically to one or more alleles of KIR3DL1 selected from *001, *016, *026, *027, *043, *052, *059, *060, *061, *064, *065, *067, *075, *002, *015, *008, *009, *020, *006, *017, *018, *022, *023, *024N, *025, *028, *029, *030, *031, *034, *035, *038, *042, *051, *054, *057, *062, *067, *074, *076, *077, *005, *041, *044, *053, *007, *032, *030, *068, *013, *010, *011, *012, *014, *045, *046, *047, *048, *049N, *050, *055, *058, *073, *004, *019, *021, *036, *037, *039, *040, *056, *063, and *072. In some embodiments, polypeptides and polypeptide formats bind specifically to the *001, *002, *007, *015, *020, and/or *033 allele of KIR3DL1.

In some embodiments, the KIR antibody agent is conjugated to a payload. In some embodiments, the payload is therapeutic (e.g., cytostatic or cytotoxic) and/or diagnostic (e.g., detectable) and may be selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof. For a chemical bond or physical bond, a functional group on the KIR antibody agent typically associates with a functional group on the payload. Alternatively, a functional group on the payload associates with a functional group on the KIR antibody agent.

The functional groups on the payload and KIR antibody agent can associate directly. For example, a functional group (e.g., a sulfhydryl group) on a payload can associate with a functional group (e.g., sulfhydryl group) on a KIR antibody agent to form a disulfide. Alternatively, the functional groups can associate through a cross-linking agent (i.e., linker). Some examples of cross-linking agents are described below. The cross-linker can be attached to either the payload or the KIR antibody agent. The number of payloads or KIR antibody agents in a conjugate is also limited by the number of functional groups present on the other. For example, the maximum number of payloads associated with a conjugate depends on the number of functional groups present on the KIR antibody agent. Alternatively, the maximum number of KIR antibody agents associated with a payload depends on the number of functional groups present on the payload.

In yet another embodiment, the conjugate comprises one KIR antibody agent associated to one payload. In one embodiment, a conjugate comprises at least one payload chemically bonded (e.g., conjugated) to at least one KIR antibody agent. The payload can be chemically bonded to a KIR antibody agent by any method known to those in the art. For example, a functional group on the payload may be directly attached to a functional group on the KIR antibody agent. Some examples of suitable functional groups include, for example, amino, carboxyl, sulfhydryl, maleimide, isocyanate, isothiocyanate and hydroxyl.

The payload may also be chemically bonded to the KIR antibody agent by means of cross-linking agents, such as dialdehydes, carbodiimides, dimaleimides, and the like. Cross-linking agents can, for example, be obtained from Pierce Biotechnology, Inc., Rockford, Ill. The Pierce Biotechnology, Inc. web-site can provide assistance. Additional cross-linking agents include the platinum cross-linking agents described in U.S. Pat. Nos. 5,580,990; 5,985,566; and 6,133,038 of Kreatech Biotechnology, B.V., Amsterdam, The Netherlands.

Alternatively, the functional group on the payload and KIR antibody agent can be the same. Homobifunctional cross-linkers are typically used to cross-link identical functional groups. Examples of homobifunctional cross-linkers include EGS (i.e., ethylene glycol bis[succinimidylsuccinate]), DSS (i.e., disuccinimidyl suberate), DMA (i.e., dimethyl adipimidate.2HCl), DTSSP (i.e., 3,3'-dithiobis[sulfosuccinimidylpropionate])), DPDPB (i.e., 1,4-di-[3'-(2'-pyridyldithio)-propionamido]butane), and BMH (i.e., bis-maleimidohexane). Such homobifunctional cross-linkers are also available from Pierce Biotechnology, Inc.

In other instances, it may be beneficial to cleave the payload from the KIR antibody agent. The web-site of Pierce Biotechnology, Inc. described above can also provide assistance to one skilled in the art in choosing suitable cross-linkers which can be cleaved by, for example, enzymes in the cell. Thus the payload can be separated from the KIR antibody agent. Examples of cleavable linkers include SMPT (i.e., 4-succinimidyloxycarbonyl-methyl-a-[2-pyridyldithio]toluene), Sulfo-LC-SPDP (i.e., sulfosuccinimidyl 6-(3-[2-pyridyldithio]-propionamido)hexanoate), LC-SPDP (i.e., succinimidyl 6-(3-[2-pyridyldithio]-propionamido)hexanoate), Sulfo-LC-SPDP (i.e., sulfosuccinimidyl 6-(3-[2-pyridyldithio]-propionamido)hexanoate), SPDP (i.e., N-succinimidyl 3-[2-pyridyldithio]-propionamidohexanoate), and AEDP (i.e., 3-[(2-aminoethyl)dithio]propionic acid HCl).

In another embodiment, a conjugate comprises at least one payload physically bonded with at least one KIR antibody agent. Any method known to those in the art can be employed to physically bond the payloads with the KIR antibody agents. For example, the KIR antibody agents and payloads can be mixed together by any method known to those in the art. The order of mixing is not important. For instance, payloads can be physically mixed with KIR antibody agents by any method known to those in the art. For example, the KIR antibody agents and payloads can be placed in a container and agitated, by for example, shaking the container, to mix the KIR antibody agents and payloads. The KIR antibody agents can be modified by any method known to those in the art. For instance, the KIR antibody agent may be modified by means of cross-linking agents or functional groups, as described above.

Multispecific Antibody Agents

The present disclosure also provides multispecific antibody body agents (e.g., bispecific antibody agents) that bind to a KIR (e.g., KIR3DL1) and at least one additional molecule. As those skilled in the art are aware, a multivalent binding agent is a molecular entity or complex that includes binding components that bind specifically to two or more targets (e.g., epitopes). Such multivalent binding agents find a variety of uses in the art, including therapeutic uses.

In some embodiments, multivalent binding agents (e.g., bispecific binding agents) provided by the present disclosure comprise antibody components. A variety of technologies are known in the art for designing, constructing, and/or producing multi-specific binding agents comprising antibody components.

For example, multivalent binding agents have been constructed that utilize a full immunoglobulin framework (e.g., IgG), a single chain variable fragment (scFv), or combinations thereof. Bispecific binding agents composed of two scFv units in tandem have been shown to be a clinically successful bispecific antibody format. For example, in the case of anti-tumor immunotherapy, bispecific binding agents that comprise two single chain variable fragments (scFvs) in tandem have been designed such that an scFv that binds a tumor antigen is linked with an scFv that engages T cells (for example, by binding CD3). In this way, T cells are recruited to a tumor site with the intention that they can mediate killing of the tumor cells (termed Bispecific T cell Engaging, or BiTE) which has been successful in preventing tumor growth in animal xenograft studies. See, e.g., Dreier et al., 2003, *J. Immunol.* 170:4397-4402; Bargou et al., 2008, *Science* 321:974-977).

In some embodiments, the present disclosure encompasses the recognition that multispecific binding agents may include a KIR antibody agent of the present disclosure to enhance NK-mediated ADCC. In some embodiments, a multispecific binding agents comprises a KIR antibody agent of the present technology and a targeting agent (e.g., a tumor targeting agent) for direct cell killing. Exemplary bispecific binding agents include those with a first antibody component specific for a NK cell (e.g., a KIR antibody agent of the present technology) and a second antibody component specific for a tumor antigen. Examples of tumor antigens include, but are not limited to, alpha fetoprotein (AFP), CA15-3, CA27-29, CA19-9, CA-125, calretinin, carcinoembryonic antigen, CD34, CD99, CD117, chromogranin, cytokeratin, desmin, epithelial membrane protein (EMA), Factor VIII, CD31 FL1, glial fibrillary acidic protein (GFAP), gross cystic disease fluid protein (GCDFP-15), HMB-45, human chorionic gonadotropin (hCG), inhibin, keratin, CD45, a lymphocyte marker, MART-1 (Melan-A), Myo D1, muscle-specific actin (MSA), neurofilament, neuron-specific enolase (NSE), placental alkaline phosphatase (PLAP), prostate-specific antigen, S100 protein, smooth muscle actin (SMA), synaptophysin, thyroglobulin, thyroid transcription factor-1, tumor M2-PK, and vimentin.

Bispecific binding agents can be made, for example, by combining heavy chains and/or light chains that recognize different epitopes of the same or different antigen. In some embodiments, by molecular function, a bispecific binding agent binds one antigen (or epitope) on one of its two binding arms (one $V_H/V_L$ pair), and binds a different antigen (or epitope) on its second arm (a different $V_H/V_L$ pair). By this definition, a bispecific binding agent has two distinct antigen binding arms (in both specificity and CDR sequences), and is monovalent for each antigen to which it binds.

In some embodiments, bispecific binding agents of the present disclosure are characterized by the ability to bind simultaneously to two targets that are of different structure. In some embodiments, bispecific binding agents of the present disclosure have at least one component that specifically binds to, for example, a NK cell (e.g., a KIR antibody agent of the present technology) and at least one other component that binds to a tumor antigen.

Bispecific binding agents (e.g., bispecific antibodies) of the present disclosure are based on the particular insight that certain formats may be more beneficial for certain targets (e.g., a tumor antigen) when employed for the diagnosis and/or treatment of a NK-related disease and/or malignancy. For example, in some embodiments, bispecific antibodies utilize a combination of scFvs having distinct binding characteristics. Bispecific antibody agents of the present disclosure may be suitable for diagnostic and/or therapeutic tumor targeting features.

In some embodiments, a bispecific binding agent (e.g., a bispecific antibody) according to the present disclosure is composed of a first binding component and a second binding component. In many embodiments, first and second binding components of a bispecific binding agent as described herein are each composed of antibody components characterized by different specificities. In some embodiments, a bispecific binding agent according to the present disclosure comprises a first binding component, a second binding component and a linker that is connected to both the first and second binding component (e.g., positioned between the first and second binding components). In various embodiments, first and/or second binding components as described herein comprise or are antibody components. In various embodiments, first and/or second binding components as described herein comprise a linker sequence.

In some embodiments, a linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide (e.g., first and/or second binding components). In some embodiments, a linker is employed in a bispecific binding agent described herein based on specific properties imparted to the bispecific binding agent such as, for example, a reduction in aggregation and/or an increase in stability. In some embodiments, a bispecific binding agent of the present disclosure comprises a $G_4S$ (SEQ ID NO: 65) linker. In some embodiments, a bispecific binding agent of the present disclosure comprises a $(G_4S)_n$ (SEQ ID NO: 66) linker, wherein n is 1, 2, 3, 4, 5, 6, 7, 8, 9, 10, 11, 12, 13, 14, 15 or more.

In some embodiments, first and/or second binding components as described herein comprise or are immunoglobulins (e.g., IgGs). In some embodiments, first and/or second binding components binding components as described herein comprise or are antibody fragments (e.g., scFvs). In some embodiments, first binding components as described herein comprise or are immunoglobulins and second binding components comprise or are antibody fragments. In some certain embodiments, first binding components are immunoglobulins and second binding components are antibody fragments. In some certain embodiments, first binding components are IgGs and second binding components are scFvs.

In some certain embodiments, a bispecific binding agent according to the present disclosure comprises a first and a second scFv. In some certain embodiments, a first scFv is linked to the C-terminal end of a second scFv. In some certain embodiments, a second scFv is linked to the C-terminal end of a first scFv. In some certain embodiments, scFvs are linked to each other via a linker sequence.

In some embodiments, a bispecific binding agent of the present disclosure comprises a heavy chain variable region with one or more CDR sequences that are listed in Table 1.

In some embodiments, a bispecific binding agent of the present disclosure comprises a heavy chain variable region with three CDR sequences that are listed in Table 1. In some embodiments, a bispecific binding agent of the present disclosure comprises a heavy chain variable region with one or more CDR sequences selected from among SEQ ID NOs: 23, 24, 25, 29, 30, 31, 35, 36, 37, 41, 42, 43, 47, 48, 49, 53, 54, 55, 59, 60 and 61. In some embodiments, a bispecific binding agent of the present disclosure comprises a heavy chain variable region with three CDR sequences selected from among SEQ ID NOs: 23, 24, 25, 29, 30, 31, 35, 36, 37, 41, 42, 43, 47, 48, 49, 53, 54, 55, 59, 60 and 61.

In some embodiments, a bispecific binding agent of the present disclosure comprises a light chain variable region with one or more CDR sequences that are listed in Table 1. In some embodiments, a bispecific binding agent of the present disclosure comprises a light chain variable region with three CDR sequences that are listed in Table 1. In some embodiments, a bispecific binding agent of the present disclosure comprises a light chain variable region with one or more CDR sequences selected from among SEQ ID NOs: 20, 21, 22, 26, 27, 28, 32, 33, 34, 38, 39, 40, 44, 45, 46, 50, 51, 52, 56, 57, and 58. In some embodiments, a bispecific binding agent of the present disclosure comprises a light chain variable region with three CDR sequences selected from among SEQ ID NOs: 20, 21, 22, 26, 27, 28, 32, 33, 34, 38, 39, 40, 44, 45, 46, 50, 51, 52, 56, 57, and 58.

In some embodiments, a bispecific binding agent of the present disclosure comprises a heavy chain variable region having sequence that is at least about 70% (e.g., at least 70%, 75%, 80%, 85%, 90%, 95%, 96%, 97%, 98%, or 99%) identical to any one of SEQ ID NO: 7, 9, 11, 13, 15, 17, and/or 19. In some embodiments, a bispecific binding agent of the present disclosure comprises a heavy chain variable region having a sequence selected from SEQ ID NOs: 7, 9, 11, 13, 15, 17, and 19. In some embodiments, a bispecific binding agent of the present disclosure comprises a light chain variable region having sequence that is at least about 70% (e.g., at least about 70%, 75%, 80%, 85%, 90%, 95%, 96%, 97%, 98%, or 99%) identical to any one of SEQ ID NO: 6, 8, 10, 12, 14, 16, and/or 18. In some embodiments, a bispecific binding agent of the present disclosure comprises a light chain variable region having a sequence selected from SEQ ID NOs: 6, 8, 10, 12, 14, 16, and 18.

In various embodiments, a first binding component of a bispecific binding agent as described herein comprises an antibody component having a sequence at least 70% (e.g., 70%, 75%, 80%, 85%, 90%, 91%, 92%, 93%, 94%, 95%, 96%, 97%, 98%, 99% or more) identical to a sequence selected from SEQ ID NOs: 7, 9, 11, 13, 15, 17, and/or 19. In various embodiments, a first binding component of a bispecific binding agent as described herein comprises an antibody component having a sequence at least 70% (e.g., 70%, 75%, 80%, 85%, 90%, 91%, 92%, 93%, 94%, 95%, 96%, 97%, 98%, 99% or more) identical to a sequence selected from SEQ ID NOs: 6, 8, 10, 12, 14, 16, and/or 18.

Nucleic Acid Construction and Expression

KIR antibody agents (e.g., KIR3DL1 antibody agents) as described herein may be produced from nucleic acid molecules using molecular biological methods known to the art. Nucleic acid molecules are inserted into a vector that is able to express the fusion proteins in when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the fusion proteins of the present disclosure under control of transcriptional/translational control signals. These methods may include in vitro recombinant DNA and synthetic techniques and in vivo recombination (See Sambrook et al., Molecular Cloning, A Laboratory Manual, Cold Spring Harbor Laboratory; Current Protocols in Molecular Biology, Eds. Ausubel, et al, Greene Publ. Assoc., Wiley-Interscience, NY).

Expression of nucleic acid molecules in accordance with the present disclosure may be regulated by a second nucleic acid sequence so that the molecule is expressed in a host transformed with the recombinant DNA molecule. For example, expression of the nucleic acid molecules of the disclosure may be controlled or regulated by a promoter and/or enhancer element, which are known in the art.

Nucleic acid constructs include regions that encode multi-specific binding proteins generated from antibodies and/or antibody components. Typically, such multi-specific binding proteins will be generated from $V_H$ and/or $V_L$ regions. After identification and selection of antibodies exhibiting desired binding and/or functional properties, variable regions of each antibody are isolated, amplified, cloned and sequenced. Modifications may be made to the $V_H$ and $V_L$ nucleotide sequences, including additions of nucleotide sequences encoding amino acids and/or carrying restriction sites, deletions of nucleotide sequences encoding amino acids, or substitutions of nucleotide sequences encoding amino acids.

Nucleic acid constructs of the present disclosure are inserted into an expression vector or viral vector by methods known to the art, and nucleic acid molecules are operatively linked to an expression control sequence.

Where appropriate, nucleic acid sequences that encode KIR antibody agents as described herein may be modified to include codons that are optimized for expression in a particular cell type or organism (e.g., see U.S. Pat. Nos. 5,670,356 and 5,874,304). Codon optimized sequences are synthetic sequences, and encode the identical polypeptide (or a biologically active fragment of a full length polypeptide which has substantially the same activity as the full length polypeptide) encoded by the non-codon optimized parent polynucleotide. In some embodiments, the coding region of the genetic material encoding antibody components, in whole or in part, may include an altered sequence to optimize codon usage for a particular cell type (e.g., a eukaryotic or prokaryotic cell). For example, the coding sequence for a human or humanized heavy (or light) chain variable region as described herein may be optimized for expression in a bacterial cells. Alternatively, the coding sequence may be optimized for expression in a mammalian cell (e.g., a CHO). Such a sequence may be described as a codon-optimized sequence.

An expression vector containing a nucleic acid molecule is transformed into a suitable host cell to allow for production of the protein encoded by the nucleic acid constructs. Exemplary host cells include prokaryotes (e.g., *E. coli*) and eukaryotes (e.g., a COS or CHO cell). Host cells transformed with an expression vector are grown under conditions permitting production of a human monoclonal antibody or a multi-specific binding agent of the present disclosure followed by recovery of the human monoclonal antibody or multi-specific binding agent.

KIR antibody agents of the present disclosure (e.g., human anti-KIR3DL1 monoclonal antibodies and fragments thereof) may be purified by any technique, which allows for the subsequent formation of a stable antibody or binding agent molecule. For example, while not wishing to be bound by theory, human monoclonal antibodies and/or multi-specific binding agents may be recovered from cells either as soluble polypeptides or as inclusion bodies, from which they may be extracted quantitatively by 8M guanidinium hydrochloride and dialysis. In order to further purify antibodies and/or multi-specific binding agents of the present disclosure, conventional ion exchange chromatography, hydrophobic interaction chromatography, reverse phase chromatography or gel filtration may be used. Human monoclonal antibodies and/or multi-specific binding agents of the present disclosure may also be recovered from conditioned media following secretion from eukaryotic or prokaryotic cells.

Administration

The present disclosure provides methods of administering an effective amount of a therapeutic active described herein (e.g., a KIR antibody agent) to a subject in need of treatment. In some embodiments, an effective amount of a KIR antibody agent of the present technology (e.g., KIR3DL1 antibody agent) or a polypeptide agent comprising the same CDRs of a KIR antibody agent as provided herein may be administered to a subject in need thereof.

Human monoclonal antibodies or multi-specific binding agents as described herein may be administered through various methods known in the art for the therapeutic delivery of agents, such as proteins or nucleic acids can be used for the therapeutic delivery of a human monoclonal antibody or multi-specific binding agent or a nucleic acid encoding a human monoclonal antibody or multi-specific binding agent of the present disclosure for killing or inhibiting growth of target cells in a subject, e.g., cellular transfection, gene therapy, direct administration with a delivery vehicle or pharmaceutically acceptable carrier, indirect delivery by providing recombinant cells comprising a nucleic acid encoding a multi-specific binding agent of the present disclosure.

Various delivery systems are known and can be used to administer a KIR antibody agent of the present disclosure, e.g., encapsulation in liposomes, microparticles, microcapsules, recombinant cells capable of expressing the compound, receptor-mediated endocytosis (see, e.g., Wu and Wu, 1987, *J. Biol. Chem.* 262:4429-4432), construction of a nucleic acid as part of a retroviral or other vector, etc. Routes of administration can be enteral or parenteral and include, but are not limited to, intravenous, subcutaneous, intramuscular, parenteral, transdermal, or transmucosal (e.g., oral or nasal). In some embodiments, KIR antibody agents of the present disclosure are administered intravenously. In some embodiments, KIR antibody agents of the present disclosure are administered subcutaneously. In some embodiments, KIR antibody agents are administered together with other biologically active agents. In some embodiments, the KIR antibody agent is administered orally, intranasally, parenterally, intravenously, intramuscularly, intraperitoneally, subcutaneously, rectally, intrathecally, intratumorally or topically.

In some embodiments, KIR antibody agents of the present disclosure (e.g., KIR3DL1 antibody agents) may be used in in vitro or in vivo screening methods where it is desirable to detect and/or measure one or more activities of a cell or cells (e.g., apoptosis or cell growth). Screening methods are well known to the art and include cell-free, cell-based, and animal assays. In vitro assays can be either solid state or soluble target molecule detection may be achieved in a number of ways known to the art, including the use of a label or detectable group capable of identifying a KIR antibody agent of the present technology which is bound to a target molecule (e.g., cell surface KIR antigen). Detectable labels may be used in conjunction with assays using human or humanized KIR antibody agents of the present disclosure.

In some embodiments, KIR antibody agents of the present disclosure (e.g., human anti-KIR3DL1 monoclonal antibodies and fragments thereof) may be used for treating diseases and/or disorders that may benefit from relieving the suppression of NK activity. In some embodiments, KIR antibody agents of the present disclosure (e.g., KIR3DL1 antibody agents) may be used for treating diseases and/or disorders that may benefit from activation of NK cells. In some embodiments, KIR antibody agents of the present disclosure (e.g., KIR3DL1 antibody agents) may be used for treating a neoplastic disease (e.g., a cancer). In some embodiments, a neoplastic disease (e.g., cancer) may be treated by administering to a patient in need thereof a therapeutically effective amount of a KIR antibody agent of the present technology, scFv, human or humanized antibody or antigen-binding fragment of thereof. In some embodiments, a cancer is acute myelogenous leukemia (AML). In some embodiments, a cancer a solid tumor, such as, for example, neuroblastoma.

In some embodiments, a cancer is a bladder cancer (e.g., a urothelial carcinoma), a brain cancer, a breast cancer (e.g., ductal carcinoma), a colorectal cancer, a endometrial cancer, a head and neck cancer, a kidney cancer (e.g., renal cell cancer, Wilms tumor), a leukemia (e.g., AML), a lung cancer (e.g, NSCLC), a melanoma, a lymphoma (e.g., non-hodgkin lymphoma, Hodgkin lymphoma), a pancreatic cancer, a prostate cancer, and/or a thyroid cancer (e.g., papillary thyroid cancer, follicular thyroid cancer, medullary thyroid cancer, anaplastic thyroid cancer). In some embodiments, a cancer is a squamous cell carcinoma, a basal cell carcinoma, or an adenocarcinoma.

The present disclosure encompasses the recognition that strong NK cell inhibition through activity of KIR3DL1 may lead to worse outcomes in certain cancer patients. The present disclosure encompasses the recognition that modulating the activity of KIR3DL1 may have clinical benefits. In some embodiments, an antibody agent that binds to KIR3DL1 may be clinically beneficially for treating cancer. The allelic combinations of KIR3DL1-h and Bw4-80I, a strongly-binding receptor-ligand combination, are enriched among patients with AML, suggesting that this genetic combination may predispose individuals to developing cancer (Shen, M., Y. Linn, and E. Ren, Immunogenetics, 2016. 68: p. 133-144). In some embodiments, an anti-KIR3DL1 antibody agent of the present disclosure blocks the inhibitory interaction between KIR3DL1 and its ligand HLA-Bw4. In some embodiments, the KIR antibody agents are administered to patients characterized by HLA-Bw4 expression. In some embodiments, the KIR3DL1 antibody agent may be administered to a patient who is HLA-Bw4+. In some embodiments, the KIR3DL1 antibody agent may be administered to a patient who is HLA-Bw4+ and has been diagnosed at one time with cancer or who is suffering from cancer.

In some embodiments, it is envisioned that inhibition of KIR3DL1 and/or particular KIR3DL1 alleles may be clinically relevant in patients with cancer, such as acute myelogenous leukemia (AML) or neuroblastoma. In some embodiments, the provided KIR antibody agents are administered to patients characterized by expression of one or more alleles of KIR3DL1, such as *001, *016, *026, *027, *043, *052, *059, *060, *061, *064, *065, *067, *075, *002, *015, *008, *009, *020, *006, *017, *018, *022, *023, *024N, *025, *028, *029, *030, *031, *034, *035, *038, *042, *051, *054, *057, *062, *067, *074, *076, *077, *005, *041, *044, *053, *007, *032, *030, *068, *013, *010, *011, *012, *014, *045, *046, *047, *048, *049N, *050, *055, *058, *073, *004, *019, *021, *036, *037, *039, *040, *056, *063, and/or *072. In some embodiments, the provided KIR antibody agents are administered to patients characterized by expression of one or more alleles of KIR3DL1 selected from: *001, *016, *026, *027, *043, *052, *059, *060, *061, *064, *065, *067, *075, *002, *015, *008, *009, *020, *006, *017, *018, *022, *023, *024N, *025, *028, *029, *030, *031, *034, *035, *038, *042, *051, *054, *057, *062, *067, *074, *076, *077, *007, *032, *030, *068, *005, *041, *044, and/or *053. In some embodiments, the provided KIR antibody agents are administered to patients characterized by expression of one or more alleles of KIR3DL1, such as *001,*002,*007, *015, *020, and *033.

In some embodiments, provided KIR antibody agents are administered to patients in whom one or more inhibitory alleles of KIR3DL1 has been detected (e.g., detected in a sample obtained from a subject). In some embodiments, one or more inhibitory alleles of KIR3DL1 is selected from *001, *016, *026, *027, *043, *052, *059, *060, *061, *064, *065, *067, *075, *002, *015, *008, *009, *020 *006, *017, *018, *022, *023, *024N, *025, *028, *029, *030, *031, *034, *035, *038, *042, *051, *054, *057, *062, *067, *074, *076, *077, *007, *032, *030, *068, *005, *041, *044, and/or *053. In some embodiments, the KIR3DL1 antibody agent is administered to patients in whom one or more inhibitory alleles of KIR3DL1 has been detected, wherein a inhibitory alleles of KIR3DL1 may include one or more of *001,*002,*007, *015, *020, and *033.

Combination Therapy

In some embodiments, therapy with a provided KIR antibody agent (e.g., a human anti-KIR3DL1 antibody agent) may be administered in combination with one or more other therapies. The at least one other therapy may be administered separately, sequentially or simultaneously. In some embodiments, the KIR3DL1 antibody agent may be administered in combination with one or more therapies that have been approved for treatment of cancer. In some embodiments, such other therapy may be or comprise a therapy that augments an immune response, such as, for example a therapy may target NK cells, γδ T cells, macrophages and/or dendritic cells. In some embodiments, such other therapy may be or comprise a therapy that relieves immune suppression (e.g., administration of one or more agents that target PD-1, CTLA-4, GD2, etc.).

In some embodiments, the KIR3DL1 antibody agent of the present technology is administered in combination with one or more therapies that would benefit from enhanced ADCC activity. In some embodiments, the KIR3DL1 antibody agent is administered in combination with one or more therapies to enhance ADCC activity. In some embodiments, one or more therapies to enhance ADCC activity may include administration of an antibody agent that can activate FcR. In some embodiments, one or more therapies to enhance ADCC activity may include administration of an agent such as, for example, rituximab (Rituxan™), trastuzumab (Herceptin®), cetuximab, anti-CD38, anti-GD2, GM-CSF, IFN-α, IFN-β, IL-2, IL-12, L-15, IL-21, anti-GITR, anti-CD47 and/or anti-PD-1. For example, the ganglioside GD2, is highly expressed on neuroectoderm-derived tumors and sarcomas, but has restricted expression on normal cells. GD2-targeting has been shown to promote NK cell activation through antibody-dependent cell-mediated cytotoxicity (ADCC) (Tarek et al., 2012, *J. Clin. Invest.*

122:3260-3270). Type I interferons (IFN-α and IFN-β) are strong stimuli for NK cells and addition of IFN-α to mAb therapy augments antitumor ADCC in vitro. (Kohrt et al., *Immunotherapy.* 2012 May; 4(5): 511-527) GM-CSF has been shown to enhance both ADCC and phagocytosis in vitro. Id.

In some embodiments, a KIR3DL1 antibody agent of the present technology is administered in combination with an anti-GD2 antibody agent. In some embodiments, a KIR3DL1 antibody agent of the present technology is administered in combination with anti-CD20 antibody agent (e.g., rituximab).

In some embodiments, a KIR3DL1 antibody agent of the present technology is administered in combination with one or more other therapeutic monoclonal antibodies to enhance ADCC in a subject who is HLA-Bw4+. In some embodiments, a subject who is HLA-Bw4+ is administered a KIR3DL1 antibody agent and an anti-GD2 antibody agent. In some embodiments, a subject who is HLA-Bw4+ is administered an anti-KIR3DL1 antibody agent and an anti-CD20 antibody agent (e.g., rituximab).

In some embodiments, a KIR3DL1 antibody agent of the present technology is administered in combination with one or more therapies that target negative regulatory pathways that inhibit immune cells. For example, earliest successful examples of such a therapeutic approach is ipilimumab for the treatment of melanoma. Ipilimumab is a monoclonal antibody (MAb) that targets CTLA-4, a key negative regulator found on activated T cells. CTLA-4 binds to members of the B7 family of accessory molecules that are expressed by dendritic cells (DCs) and other antigen presenting cells (APCs). Binding of CTLA-4 to these accessory molecules effectively inhibits further T cell activation and expansion, thereby blocking the progress of an immune response involving such cells (Mellman et al., 2011 *Nature* 480:480-489). By targeting CTLA-4, ipilimumab releases this inhibition, permitting activation and expansion of T cells, including specifically those that destroy cancer cells. Other approaches that have been pursued to treat cancer by removing immune inhibition include targeting the Programmed Death-1 (PD-1) T cell co-receptor and its ligands B7-H1/PD-L1 and B7-DC/PD-L2, which are part of a pathway that maintains an immunosuppressive tumor microenvironment (Topalian et al., 2012 *Curr. Opin. Immunol.* 24:207-212). In particular, Phase I/II clinical trials using anti-PD-1 (Topalian et al., 2012 *N. Engl. J. Med.* 366:2443-2454) or anti-PD-L1 (Brahmer et al., 2012 *N. Engl. J. Med.* 366:2455-2465) antibodies have demonstrated tumor regression or stabilization in melanoma, non-small cell lung cancer, renal cell carcinoma and ovarian cancer.

In some embodiments, a KIR3DL1 antibody agent of the present technology is administered in combination with one or more therapies that activate immune cells in a subject who is HLA-Bw4+. In some embodiments, a KIR3DL1 antibody agent of the present technology is administered in combination with an anti-GD2 antibody agent to a subject who is HLA-Bw4+. In some embodiments, a KIR3DL1 antibody agent of the present technology is administered in combination with an anti-PD-1 antibody agent to a subject who is HLA-Bw4+. In some embodiments, a KIR3DL1 antibody agent of the present technology is administered in combination with a CTLA-4 antibody agent to a subject who is HLA-Bw4+.

In some embodiments, a KIR3DL1 antibody agent of the present technology is administered in combination with one or more therapies that have been approved for treatment of AML, such as, for example, arsenic trioxide, Cerubidine (daunorubicin hydrochloride), Clafen (cyclophosphamide), cyclophosphamide, Cytarabine, Cytosar-U (cytarabine), Cytoxan (cyclophosphamide), daunorubicin hydrochloride, doxorubicin hydrochloride, Idamycin (idarubicin hydrochloride), Idarubicin hydrochloride, mitoxantrone hydrochloride, Neosar (cyclophosphamide), Rubidomycin (daunorubicin hydrochloride), Tabloid (thioguanine), Tarabine PFS (cytarabine), Thioguanine, Trisenox (arsenic trioxide), Vincasar PFS (vincristine sulfate), and/or vincristine sulfate.

Pharmaceutical Compositions

The present disclosure further provides pharmaceutical compositions comprising KIR antibody agents of the present disclosure (e.g., a KIR3DL1 antibody agent) and a pharmaceutically acceptable carrier or excipient. The composition, if desired, can also contain one or more additional therapeutically active substances.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

For example, pharmaceutical compositions provided here may be provided in a sterile injectable form (e.g., a form that is suitable for subcutaneous injection or intravenous infusion). For example, in some embodiments, pharmaceutical compositions are provided in a liquid dosage form that is suitable for injection. In some embodiments, pharmaceutical compositions are provided as powders (e.g., lyophilized and/or sterilized), optionally under vacuum, which are reconstituted with an aqueous diluent (e.g., water, buffer, salt solution, etc.) prior to injection. In some embodiments, pharmaceutical compositions are diluted and/or reconstituted in water, sodium chloride solution, sodium acetate solution, benzyl alcohol solution, phosphate buffered saline, etc. In some embodiments, powder should be mixed gently with the aqueous diluent (e.g., not shaken).

Formulations of the pharmaceutical compositions described herein may be prepared by any method known or hereafter developed in the art of pharmacology. In general, such preparatory methods include the step of bringing the active ingredient into association with a diluent or another excipient and/or one or more other accessory ingredients, and then, if necessary and/or desirable, shaping and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100% (w/w) active ingredient.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this disclosure.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by the United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical formulations. Excipients such as cocoa butter and suppository waxes, coloring agents, coating agents, sweetening, flavoring, and/or perfuming agents can be present in the composition, according to the judgment of the formulator.

In some embodiments, provided pharmaceutical compositions comprise one or more pharmaceutically acceptable excipients (e.g., preservative, inert diluent, dispersing agent, surface active agent and/or emulsifier, buffering agent, etc.). In some embodiments, pharmaceutical compositions comprise one or more preservatives. In some embodiments, pharmaceutical compositions comprise no preservative.

In some embodiments, pharmaceutical compositions are provided in a form that can be refrigerated and/or frozen. In some embodiments, pharmaceutical compositions are provided in a form that cannot be refrigerated and/or frozen. In some embodiments, reconstituted solutions and/or liquid dosage forms may be stored for a certain period of time after reconstitution (e.g., 2 hours, 12 hours, 24 hours, 2 days, 5 days, 7 days, 10 days, 2 weeks, a month, two months, or longer). In some embodiments, storage of antibody compositions for longer than the specified time results in antibody degradation.

Liquid dosage forms and/or reconstituted solutions may comprise particulate matter and/or discoloration prior to administration. In some embodiments, a solution should not be used if discolored or cloudy and/or if particulate matter remains after filtration.

General considerations in the formulation and/or manufacture of pharmaceutical agents may be found, for example, in Remington: The Science and Practice of Pharmacy 21st ed., Lippincott Williams & Wilkins, 2005.

Kits

The present disclosure further provides kits comprising at least one KIR antibody agent (e.g., KIR3DL1 antibody agent) as described herein for the detection of a KIR protein (e.g., KIR3DL1) and/or treatment of cancer. Kits may be used in any applicable method, including, for example, therapeutically, diagnostically, etc., and may further comprise instructions for use. Instructions for use can be a notice in the form prescribed by a governmental agency regulating the manufacture, use or sale of pharmaceuticals or biological products, which notice reflects (a) approval by the agency of manufacture, use or sale for human administration, (b) directions for use, or both.

The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The kit may further comprise a second container which holds a diluent suitable for diluting the pharmaceutical composition towards a higher volume. Suitable diluents include, but are not limited to, the pharmaceutically acceptable excipient of the pharmaceutical composition and a saline solution. Furthermore, the kit may comprise instructions for diluting the pharmaceutical composition and/or instructions for administering the pharmaceutical composition, whether diluted or not. The containers may be formed from a variety of materials such as glass or plastic and may have a sterile access port (for example, the container may be an intravenous solution bag or a vial having a stopper which may be pierced by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. The kits may optionally include instructions customarily included in commercial packages of therapeutic or diagnostic products, that contain information about, for example, the indications, usage, dosage, manufacture, administration, contraindications and/or warnings concerning the use of such therapeutic or diagnostic products.

The kits may be useful for detecting the presence of an immunoreactive KIR3DL1 protein in a biological sample, e.g., any body fluid including, but not limited to, e.g., serum, plasma, lymph, cystic fluid, urine, stool, cerebrospinal fluid, ascitic fluid or blood and including biopsy samples of body tissue. For example, the kit can comprise: one or more KIR3DL1 antibody agents described herein capable of binding a KIR3DL1 protein in a biological sample; means for determining the amount of the KIR3DL1 protein in the sample; and means for comparing the amount of the immunoreactive KIR3DL1 protein in the sample with a standard. One or more of the anti-KIR3DL1 antibody agents may be labeled. The kit components, (e.g., reagents) can be packaged in a suitable container. The kit can further comprise instructions for using the kit to detect the immunoreactive KIR3DL1 protein.

For antibody-based kits, the kit can comprise, e.g., 1) a first antibody, e.g., a KIR3DL1 antibody agent of the present technology, attached to a solid support, which binds to a KIR3DL1 protein; and, optionally; 2) a second, different antibody which binds to either the KIR3DL1 protein or to the first antibody, and is conjugated to one or more detectable labels. In one embodiment, the one or more detectable labels comprise a radioactive label, a fluorescent label, or a chromogenic label. Additionally or alternatively, in some embodiments, the kit further comprises a secondary antibody that specifically binds to an antibody agent described herein. In some embodiments, the secondary antibody is coupled to at least one detectable label selected from the group consisting of a radioactive label, a fluorescent label, or a chromogenic label.

The kit can also comprise, e.g., a buffering agent, a preservative or a protein-stabilizing agent. The kit can further comprise components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit, e.g., for detection of a KIR3DL1 protein in vitro or in vivo, or for treatment of cancer in a subject in need thereof. In certain embodiments, the use of the reagents can be according to the methods of the present technology.

Other features of the disclosure will become apparent in the course of the following descriptions of exemplary embodiments, which are given for illustration of the disclosure and are not intended to be limiting thereof.

EXAMPLES

The following examples are provided to illustrate, but not limit the claimed disclosure.

Example 1—KIR3DL1 Antibody Agents

Among other things, the present disclosure describes the development of antibodies that specifically bind to particular subtypes and/or alleles of KIR3D. Specifically, this example describes development of human IgG monoclonal antibodies that bind with high affinity to different KIR3DL1 alleles. Soluble KIR3DL1-Fc constructs were created with an IL-2 leader sequence and the extracellular domains of various cell-surface expressed KIR3DL1 alleles (e.g., KIR3DL1*001, *002,*007/015, *020, *033 alleles) fused with an Fc domain. Protein sequences of the extracellular domains of these exemplary KIR3DL1 alleles are provided below.

```
Protein sequence: KIR3DL1*001
                                                   SEQ ID NO: 1
HMGGQDKPFLSAWPSAVVPRGGHVTLRCHYRHRFNNFMLYKEDRIHIPIFHGR

IFQESFNMSPVTTAHAGNYTCRGSHPHSPTGWSAPSNPVVIMVTGNHRKPSLLA

HPGPLVKSGERVILQCWSDIMFEEIFFLHKEGISKDPSRLVGQIHDGVSKANFSIG

PMMLALAGTYRCYGSVTHTPYQLSAPSDPLDIVVTGPYEKPSLSAQPGPKVQA

GESVTLSCSSRSSYDMYHLSREGGAHERRLPAVRKVNRTFQADFPLGPATHGG

TYRCFGSFRHSPYEWSDPSDPLLVSVTGNPSSSWPSPTEPSSKSGNPRHLH

Protein sequence: KIR3DL1*002
                                                   SEQ ID NO: 2
HVGGQDKPFLSAWPSAVVPRGGHVTLRCHYRHRFNNFMLYKEDRIHVPIFHGR

LFQESFNMSPVTTAHAGNYTCRGSHPHSPTGWSAPSNPVVIMVTGNHRKPSLL

AHPGPLVKSGERVILQCWSDIMFEHFFLHKEGISKDPSRLVGQIHDGVSKANFSI

GPMMLALAGTYRCYGSVTHTPYQLSAPSDPLDIVVTGPYEKPSLSAQPGPKVQ

AGESVTLSCSSRSSYDMYHLSRERGAHERRLPAVRKVNRTFQADFPLGPATHG

GTYRCFGSFRHSPYEWSDPSDPLLVSVTGNPSSSWPSPTEPSSKSGNPRH

Protein sequence: KIR3DL1*007/015
                                                   SEQ ID NO: 3
HVGGQDKPFLSAWPSAVVPRGGHVTLRCHYRHRFNNFMLYKEDRIHVPIFHGR

LFQESFNMSPVTTAHAGNYTCRGSHPHSPTGWSAPSNPVVIMVTGNHRKPSLL

AHPGPLVKSGERVILQCWSDIMFEHFFLHKEGISKDPSRLVGQIHDGVSKANFSI

GPMMLALAGTYRCYGSVTHTPYQLSAPSDPLDIVVTGPYEKPSLSAQPGPKVQ

AGESVTLSCSSRSSYDMYHLSRERGAHERRLPAVRKVNRTFQADFPLGPATHG

GTYRCFGSFRHSPYEWSDPSDPLLVSVTGNPSSSWPSPTEPSSKSGNPRH

Protein sequence: KIR3DL1*020
                                                   SEQ ID NO: 4
HVGGQDKPFLSAWPSAVVPRGGHVTLRCHYRHRFNNFMLYKEDRIHVPIFHGR

LFQESFNMSPVTTAHAGNYTCRGSHPHSPTGWSAPSNPVVIMVTGNHRKPSLL
```

```
AHPGPLVKSGERVILQCWSDIMFEHFFLHKEGISKDPSSLVGQIHDGVSKANFSI

GPMMLALAGTYRCYGSVTHTPYQLSAPSDPLDIVVTGPYEKPSLSAQPGPKVQ

AGESVTLSCSSRSSYDMYHLSREGGAHERRLPAVRKVNRTFQADFPLGPATHG

GTYRCFGSFRHSPYEWSDPSDPLLVSVTGNPSSSWPSPTEPSSKSGNPRHL

Protein sequence: KIR3DL1*033
                                                          SEQ ID NO: 5
HVGGQDKPFLSAWPSAVVPRGGHVTLRCHYRHRFNNFMLYKEDRIHVPIFHGR

LFQESFNMSPVTTAHAGNYTCRGSHPHSPTGWSAPSNPVVIMVTGNHRKPSLL

AHPGPLVKSGERVILQCWSDIMFEHFFLHKEGISEDPSRLVGQIHDGVSKANFSI

GPMMLALAGTYRCYGSVTHTPYQLSAPSDPLDIVVTGPYEKPSLSAQPGPKVQ

AGESVTLSCSSRSSYDMYHLSREGGAHERRLPAVRKVNRTFQADFPLGPATHG

GTYRCFGSFRHSPYEWSDPSDPLLVSVTGNPSSSWPSPTEPSSKSGNPRHLH
```

The soluble KIR3DL1 fusion proteins were used to pan against a human scFv antibody phage display library. Seven human antibody clones were selected for further characterization: ET160-42, ET160-61, ET160-72, ET160-73, ET160-74, ET160-77, ET160-80 (ET160-42, ET160-61, ET160-72, ET160-73, ET160-74, ET160-77, ET160-80 antibodies are abbreviated in the Figures as 42, 61, 72, 73, 74, 77, 80, respectively). The amino acid sequences for the variable domains of the candidate anti-KIR3DL1 human antibody clones are listed below. The sequences of the CDRs are underlined in the amino acid sequence for each candidate.

```
ET160-42 Lv (lambda)
                                                          SEQ ID NO: 6
QSALTQPASVSGSPGQSITISCTGTSSDVGGYNYVSWYQQHPGKAPKLMIYDVS

NRPSGVSNRFSGSKSGNTASLTISGLQAEDEADYYCSSYTSSNTLVFGTGTKVT

VLG

ET160-42 Hv
                                                          SEQ ID NO: 7
QVQLVQSGAEVKKPGASVKVSCKASGYTFTGYYMHWVRQAPGQGLEWMGW

INPNSGGTNYAQKFQGRVTMTRDTSISTAYMELSRLRSDDTAVYYCADLFYWG

QGTLVTVSS

ET160-61 Lv (lambda)
                                                          SEQ ID NO: 8
NFMLTQPLSVSESPGKTVTISCTANGGSLASKYVQWFQQRPGSSPTTVIYDDNL

RPSGVPDRFSGSIDTSSNSAALTISGLKTEDEADYYCQSYDNSSVVFGGGTKLTV

LG

ET160-61 Hv
                                                          SEQ ID NO: 9
QVQLVESGGGLVQPGRSLRLSCAASGFTFDDYAMHWVRQAPGKGLEWVSGIS

WNSGSIGYADSVKGRFTISRDNAKNSLYLQMNSLRAEDTAVYYCASSLRYFEW

PIDYWGQGTLVTVSS

ET160-72 Lv (lambda)
                                                          SEQ ID NO: 10
LPVLTQPPSISGAPRQRVTISCSGARSNIGNNAVNWYQQVPGEAPKLLIFYDDQ

QPSGISGRFSGSKSGTSASLAISGLQSEDEADYYCAAWDDSLNGWVFGGGTKL

TVLG

ET160-72 Hv
                                                          SEQ ID NO: 11
QVQLVQSGGGVVRSGGSLRLTCAASGFTFGDYGMSWVRQAPGKGLEWVSGIN

WNGGGTGYADSVKGRFTISRDNAKDSLYLQMNSLRAEDTALYYCARVWGCG

STTCYEGADDAFDIWGQGTMVTVSS
```

ET160-73 Lv (kappa) SEQ ID NO: 12
DVVMTQSPLSLPVTLGQPASISCRST<u>QSLVHSDGNTYL</u>NWFQQRPGQSPRRLIY
<u>GVS</u>NRDFGVPDRFSASGSGTDFTLKINRVEAEDVGVYYC<u>MQGTHWPLT</u>FGQG
TKVEIKR ET160-73 Hv SEQ ID NO: 13
QVQLVQSGAEVKKPGESLKISCKGS<u>GYSFTSYW</u>IGWVRQMPGKGLEWMGI<u>IYP
GDSDT</u>RYSPSFQGQVTISADKSISTAYLQWSSLKASDTAMYYC<u>ARGREQLWLD
GMDV</u>WGQGTTVTVSS ET160-74 Lv (lambda) SEQ ID NO: 14
QSVLTQPPSVSAAPGQKVTISCSGS<u>SSNVGNNY</u>VSWYQQVPGTAPKLLIY<u>DNNR</u>
RPSGIPDRFSGSKSGTSATLGITGLQTGDEADYYC<u>GTWDNSLRVEL</u>FGGGTKVT
VLG ET160-74 Hv SEQ ID NO: 15
QVQLVQSGAEVKKPGSSVKVSCKAS<u>GGTFSSYAI</u>SWVRQAPGQGLEWMGW<u>M
NPNSGNT</u>GYAQKFQGRVTMTRNTSISTAYMELSSLRSEDTAVYYC<u>ARYSFHLD
GW</u>GQGTLVTVSS ET160-77 Lv (lambda) SEQ ID NO: 16
SYELTQPPSVSVAPGQAATITCAGD<u>NIESKS</u>VNWYQQKPGQAPVLVVY<u>DDTVR</u>
PSGIPERFSGSNSGNPATLTISRSEAGDEADYYC<u>QVWDNRRDHVV</u>FGGGTKVT
VLG ET160-77 Hv SEQ ID NO: 17
EVQLVETGGGLVKPGGSLRLSCAAS<u>GFTFSDYYMS</u>WIRQAPGKGLEWVSY<u>ISS
SSSYT</u>NYADSVKGRFTISRDNAKNSLYLQMNSLRAEDTAVYYC<u>AREGIAAADA
FDI</u>WGQGTMVTVSS ET160-80 Lv (lambda) SEQ ID NO: 18
QAVVTQEPSLTVSPGGTVTLTCGSST<u>GAVTSGHY</u>PYWFQQKPGQAPRTLIY<u>ETS</u>
NKYSWTPARFSGSLLGGKAALTLSGAQPEDEAEYHC<u>FLSYSGTVV</u>FGGGTKLT
VLG ET160-80 Hv SEQ ID NO: 19
QMQLVQSGAEVKKPGASVKVSCKAS<u>GYTFTGYY</u>MEIWVRQAPGQGLEWMGR
<u>INPNSGGT</u>NYAQKFQGRVTMTRDTSISTAYMELSRLRSDDTAVYYC<u>ARYGDW</u>
GQGTLVTVSS

Example 2—In Vitro Binding of KIR3DL1 Antibody Agents

This Example describes the in vitro binding properties of exemplary anti-KIR3DL1 antibody agents.

These seven candidate KIR3DL1 antibody clones exhibit a binding specificity ($K_D$) for the KIR3DL1 alleles in a range of 4.1 nM to 22.7 nM, as determined using the ForteBio QK system (Pall ForteBio LLC, Fremont Calif.). The binding specificities for each of the candidate anti-KIR3DL1 antibodies for the different KIR3DL1 allotypes is listed in Table 2.

TABLE 2

Binding affinity of ET160 antibodies (hIgG1) towards different alleles of CD158e, shown as $K_D$ (nM) and as assayed by Forte-Bio

| Antibody | KIR3DL1 allele 001 | KIR3DL1 allele 002 | KIR3DL1 allele 007/015 | KIR3DL1 allele 020 | KIR3DL1 allele 033 |
|---|---|---|---|---|---|
| ET160-42 | 12.9 | 8.5 | 8.4 | 10.1 | 10.3 |
| ET160-61 | 15.1 | 21.7 | 4.1 | 19.4 | 22.7 |
| ET160-72 | 15.8 | 11.6 | 11.6 | 11.4 | 15.4 |
| ET160-73 | 21.2 | 16.3 | 16.1 | 15.7 | 14.4 |
| ET160-74 | 13.3 | 8.6 | 10.1 | 11.2 | 11.0 |

TABLE 2-continued

Binding affinity of ET160 antibodies (hIgG1) towards different alleles of CD158e, shown as $K_D$ (nM) and as assayed by Forte-Bio

| Antibody | KIR3DL1 allele 001 | KIR3DL1 allele 002 | KIR3DL1 allele 007/015 | KIR3DL1 allele 020 | KIR3DL1 allele 033 |
|---|---|---|---|---|---|
| ET160-77 | 13.9 | 10.9 | 11.4 | 10.5 | 13.1 |
| ET160-80 | 12.0 | 10.3 | 11.2 | 9.5 | 11.2 |

The seven candidate KIR3DL1 antibody clones (Table 1) each bound soluble extracellular KIR3DL1 alleles *001, *002, *007/015, *020, and *033 (SEQ ID NOs:1-5). The binding parameters for each antibody were determined for the KIR3DL1 allele-001 antigen and are provided in Table 3.

TABLE 3

Binding parameters (Partial Fit) for ET160 IgG antibodies vs. KIR3DL1 allele-001 antigen (Forte-Bio)

| Antibody | $k_d$ [1/s] | Error in $k_d$ [1/s] | $k_a$ [1/Ms] | $K_D$ [nM] |
|---|---|---|---|---|
| ET160-42 | 2.21E-3 | 9.21E-5 | 1.72E5 | 12.9 |
| ET160-61 | 1.93E-3 | 1.49E-4 | 1.27E5 | 15.1 |
| ET160-72 | 2.12E-3 | 7.41E-5 | 1.34E5 | 15.8 |
| ET160-73 | 3.02E-3 | 5.13E-5 | 1.43E5 | 21.2 |
| ET160-74 | 1.61E-3 | 1.30E-4 | 1.22E5 | 13.3 |
| ET160-77 | 2.22E-3 | 7.46E-5 | 1.60E5 | 13.9 |
| ET160-80 | 1.86E-3 | 9.32E-5 | 1.55E5 | 12.0 |

Additional binding studies with Biacore confirmed variable affinities of the antibody clones for different KIR3DL1 proteins. See, Tables 4 and 5.

TABLE 4

Affinity ($K_D$ in nM) using BIACORE (T-100) with KIR3DL1 alleles 001, 002 and 033

| Antibody | Allele 001 | Allele 002 | Allele 033 |
|---|---|---|---|
| ET160-42 | 89.5 | 93.5 | 75.2 |
| ET160-61 | 45.9 | 27.7 | 10.8 |
| ET160-72 | 182.3 | 315.9 | 137.9 |
| ET160-73 | 136.3 | 123.8 | 55.6 |
| ET160-74 | 11.9 | 108.4 | 62.2 |
| ET160-77 | 53.1 | 197.4 | 48.3 |
| ET160-80 | 85.0 | 88.2 | 84.4 |
| DX9 (PHB4385) | 14.1 | 30.6 | 8.6 |

TABLE 5

Binding kinetics using BIACORE (T-100) on Allele 002

| Antibody | $k_{on}$ (1/Ms) | $k_{off}$ (1/s) | $K_D = k_{off}/k_{on}$ (M) | $K_D$ (nM) |
|---|---|---|---|---|
| ET160-42 | 1.83E+05 | 1.71E-02 | 9.35E-08 | 93.5 |
| ET160-61 | 8.40E+04 | 2.32E-03 | 2.77E-08 | 27.7 |
| ET160-72 | 5.05E+04 | 1.59E-02 | 3.16E-07 | 315.9 |
| ET160-73 | 3.89E+04 | 4.81E-03 | 1.24E-07 | 123.8 |
| ET160-74 | 1.03E+05 | 1.12E-02 | 1.08E-07 | 108.4 |
| ET160-77 | 5.00E+04 | 9.87E-03 | 1.97E-07 | 197.4 |
| ET160-80 | 2.12E+05 | 1.87E-02 | 8.82E-08 | 88.2 |
| DX9 (PHB4385) | 3.24E+04 | 9.92E-04 | 3.06E-08 | 30.6 |

Additionally, primary NK cells were stained with fluorescein-tagged KIR3DL1 monoclonal antibodies. This staining demonstrated specificity of the fluorescein-tagged KIR3DL1 monoclonal antibodies for NK cells with surface expression of inhibitory KIR (high- and low-expressing isoforms) (data not shown). Importantly, no staining of NK cells with the activating KIR3DS1 or with the null protein KIR3DL1*004, which is intracellulary retained (data not shown) and (Pando, M., et al., *J. Immunol.,* 2003. 171: p. 6640-6649), was observed with the fluorescein-tagged KIR3DL1 monoclonal antibodies. These in vitro studies demonstrate the high level of specificity of the humanized IgG1 antibodies for surface-expressed KIR3DL1, irrespective of allotypes or isoforms. The results demonstrate that the antibody agents of the present technology are useful for detecting inhibitory KIR (high- and low-expressing isoforms) in a sample.

Example 3—Competitive Binding KIR3DL1 Antibody Agents

This Example describes competitive binding of exemplary anti-KIR3DL1 antibody agents to KIR3DL1. Specifically, exemplary KIR3DL1 antibody agents were tested at increasing concentrations for their ability to compete with binding of KIR3DL1*001-Fc to HLA-B*44:03 on the surface of 721.221 cells. With the exception of clone ET160-77, they all competed with binding of soluble KIR3DL1 to the B*44 transfected cell line. See FIG. 1.

Figure 2:
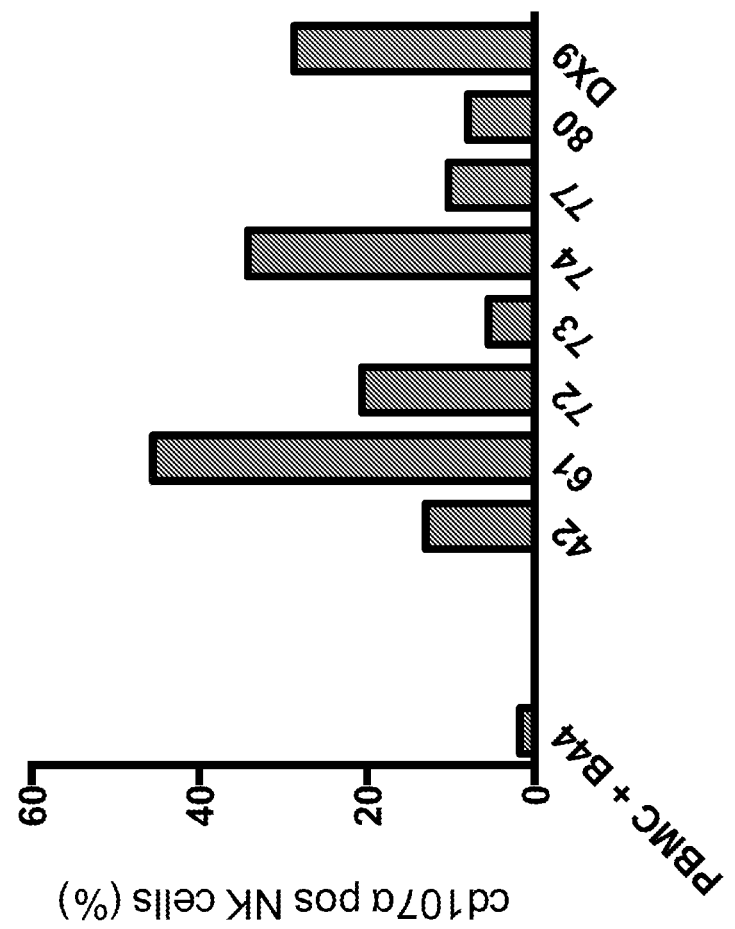
FIG. 2 depicts NK cell activation in the HLA-null cell line 721.221 transfected with the Bw4-epitope expressing HLA-B*44:03 allele in the presence of various anti-KIR3DL1 human IgG1 antibodies. NK cell activation was assessed by measuring CD107a degranulation (y-axis, CD107α positive NK cells). Comparison is made to the murine anti-KIR3DL1 blocking antibody DX9.

Initial in vitro studies examined the ability of the blocking antibodies to disrupt the engagement of KIR3DL1 on primary NK cells by HLA-Bw4 carried on target cells. 721.221 is an NK-sensitive cell line which directly activates NK cells leading to CD107a mobilization, a marker of degranulation. However, when transfected with the Bw4(+)HLA-B*44:03 allele, the resultant transfectant (Bw4(+) 721.221) could now inhibit KIR3DL1(+) NK cells (FIG. 2, "PBMC+B44). Addition of the individual human IgG1 anti-KIR3DL1 antibodies led to the activation of the NK cells, as measured by CD107a mobilization (FIG. 2). The degree of rescue of NK activation was variable; at least two antibodies of the present technology were able to elicit an NK activation response superior to that observed with the murine anti-KIR3DL1 DX9 antibody.

Figure 3:
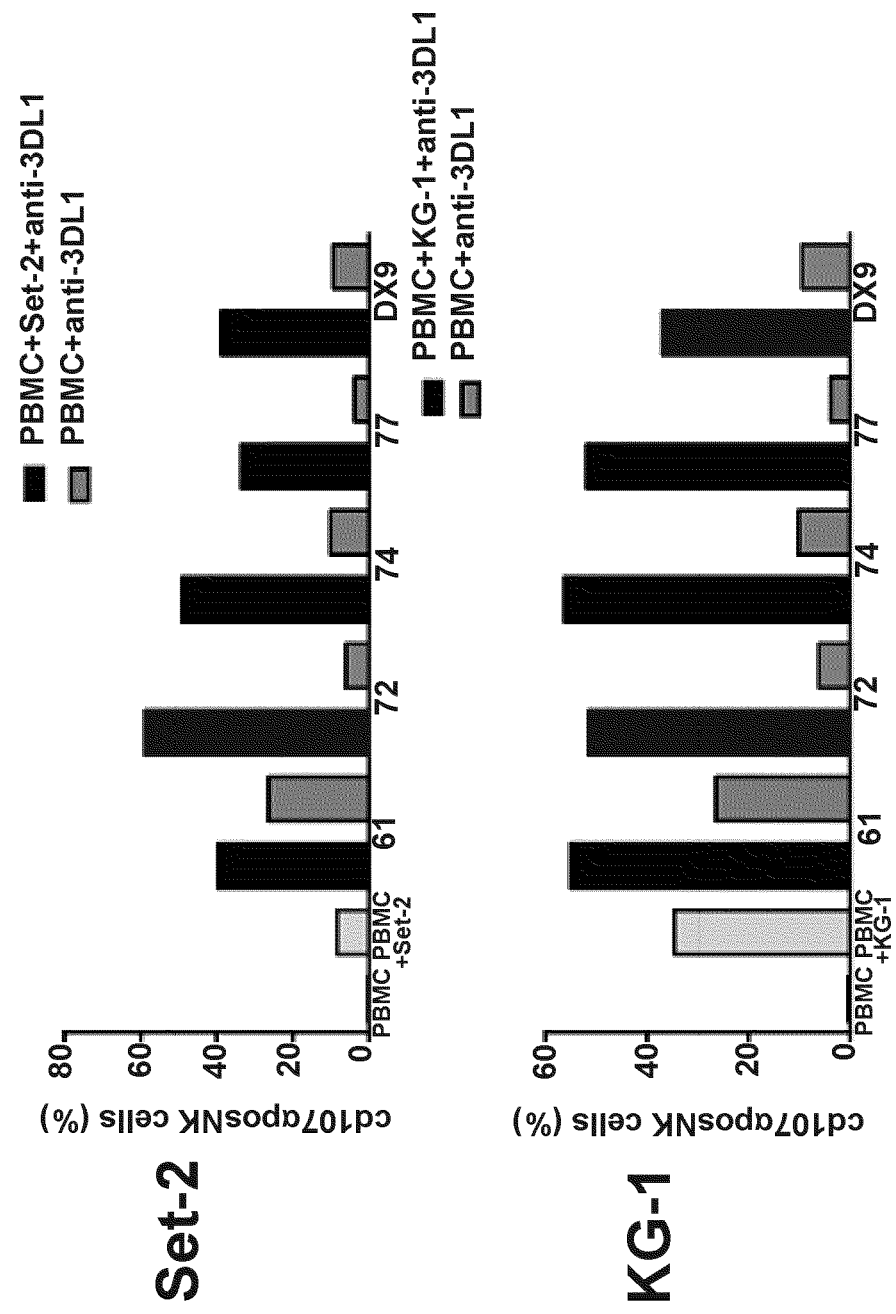
FIG. 3 depicts NK cell activation by KIR3DL1 antibody agents as measured during NK:target cell cocultures. Addition of anti-KIR3DL1 monoclonal antibodies to PBMC cultures results in high NK activation in the presence of the HLA-Bw4+ leukemia target cells, SET-2 and KG-1 (black bars in top and bottom panels). NK inhibition is caused by KIR3DL1-HLA-Bw4+ binding. Activation in the presence of the murine DX9 anti-KIR3DL1 antibody is shown for comparison. The enhanced activation is due to release of NK cells from the inhibition state that is observed in the absence of anti-KIR3DL1 antibody (light grey bars). Co-incubation of antibody with NK cells alone leads to no or low non-specific NK activation (dark grey bars).

To assess whether the candidate anti-KIR3DL1 monoclonal antibodies can interfere with HLA-Bw4 inhibition by leukemia target cells, Set-2 and KG-1, two acute myelogenous leukemia cell lines that express HLA-Bw4, were used as target cells. Peripheral blood mononuclear cells were incubated with either Set-2 or KG-1 and monitored for baseline NK activation, as measured by CD107a mobilization. There was baseline inhibition of NK cells by the leukemia target cells, as evidenced by the poor percentage of CD107a+ NK cells co-incubated with the target cell (FIG. 3, light grey bars). Upon addition of the IgG1 anti-KIR3DL1 monoclonal antibodies, however, the percentage of CD107a+ NK increased significantly (FIG. 3, black bars). Furthermore, with the exception of clone ET160-61, there appeared to be no background stimulation of NK cells by the anti-KIR3DL1 antibodies, when the clones were co-incubated with NK but in the absence of leukemia target (FIG. 3, dark grey bars). Nonspecific NK stimulation by ET160-61, however, was comparatively low in relation to the high NK stimulation in the presence of antibody and leukemia target cell (FIG. 3, black bars). The results demonstrate that the antibody agents of the present technology are useful for treating cancer in a subject in need thereof.

Example 4—KIR3DL1 Antibody Agents Killing of Target Cells

This Example describes in vitro cell killing mediated by KIR3DL1 antibody agents. While CD107a granule mobilization is a well-characterized marker of NK activation, killing of target cells is considered a more accurate measure of true cell mediated cytotoxicity. This is particularly relevant when one considers that NK cells are known to be "serial killers," implying that even if not all NK cells are activated (e.g., KIR3DL1 expression occurs on a fraction of NK cells and not the entire NK population), those that are activated can kill multiple target cells, leading to significant tumor cytotoxicity. It is important to note that the anti-KIR2DL therapeutic monoclonal antibody can lead to higher NK activation as measured by CD107a mobilization, but is ineffective at killing target cells in prolonged cytotoxicity assays, due to antibody-induced trogocytosis by neighboring macrophages and disarming of NK effector function (Carlsten, M., et al., Clin. Cancer Res., 2016. 22: p. 5211-5222).

Figure 4:
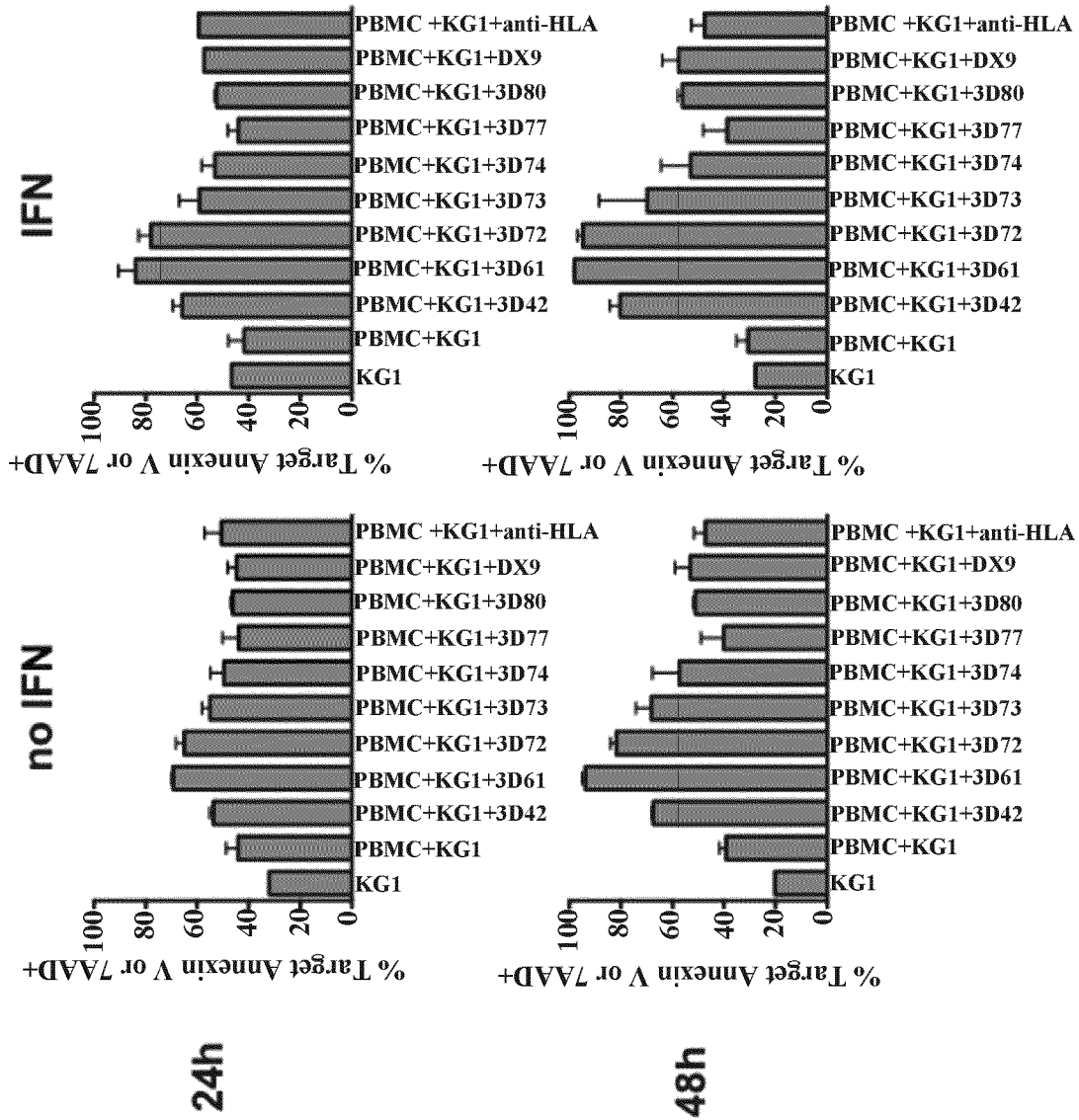
FIG. 4 depicts killing of KG-1 myeloid leukemia cells in the presence of NK cells alone (PBMC+KG1) or in the presence of NK cells (PBMC+KG1) and anti-KIR3DL1 antibody. Control conditions include (PBMC+KG1 target cell+murine anti-KIR3DL1 DX9) and (PBMC+KG1 target cell+anti-HLA antibody). Cell killing was assessed in the presence or absence of extrinsic IFN-γ.

The ability of NK cells to kill leukemia target cells in the presence of the IgG1 anti-KIR3DL1 monoclonal antibodies was measured. FIG. 4 depicts the percent of dead cells among KG-1 leukemia target cells, as measured by Annexin V or 7-AAD staining, after incubation in different conditions for 24 and 48 hours. Spontaneous cell death at 24 and 48 hours in KG-1 leukemia target cells alone was measured at 20-30%. Incubation of targets with PBMC also led to modestly higher tumor killing, presumably due to the presence of NK cells. The addition of candidate IgG1 anti-KIR3DL1 antibody agents, however, increased killing of the KG-1 leukemia population. For example, for certain IgG1 anti-KIR3DL1 antibody agents killing of the KG-1 leukemia cell population was increased up to 70% at 24 hours and to nearly 100% at 48 hours. Prior incubation of the HLA-Bw4+ leukemia target with extrinsic IFN-γ, which induces upregulation of HLA class I expression on the target cell, did not affect the enhanced ability of the NK cells to kill target cells in the presence of the blocking antibodies. This is likely due to intrinsic IFN-γ release into the media from activated NK cells, as previously demonstrated in Tarek, N., et al., J. Clin. Invest., 2012. 122: p. 3260-3270.

The highest leukemia killing was observed with clone ET160-61, the clone that demonstrated some non-specific NK activation when incubated with KIR3DL1(+) NK cells and may therefore be useful as an NK activator against leukemia targets.

Several anti-KIR3DL1 human monoclonal antibodies (e.g., candidates ET160-61, ET160-72 and ET160-73) are more effective than the tested control pan anti-HLA antibody in releasing NK cells from inhibition and augmenting killing of target cells (FIG. 4).

Together, these findings demonstrate the ability of the antibodies of the present technology to enhance leukemia killing, making the antibodies highly suitable as a therapeutic agent in the treatment of leukemia, in particular myelogenous leukemias and pre-leukemic conditions such as myelodysplastic syndrome. With respect to interference with HLA-Bw4 interaction with KIR3DL1, at least some of the antibodies of the present technology (e.g., ET160-61) may also enhance NK killing of target cancer cells regardless of HLA expression possibly through KIR3DL1-mediated NK activation, making the antibodies potentially useful also in individuals negative for HLA-Bw4. Because the overwhelming majority of individuals express alleles of KIR3DL1 on the NK cell surface, nearly all patients may therefore benefit from the enhanced NK activity.

Figure 5A:
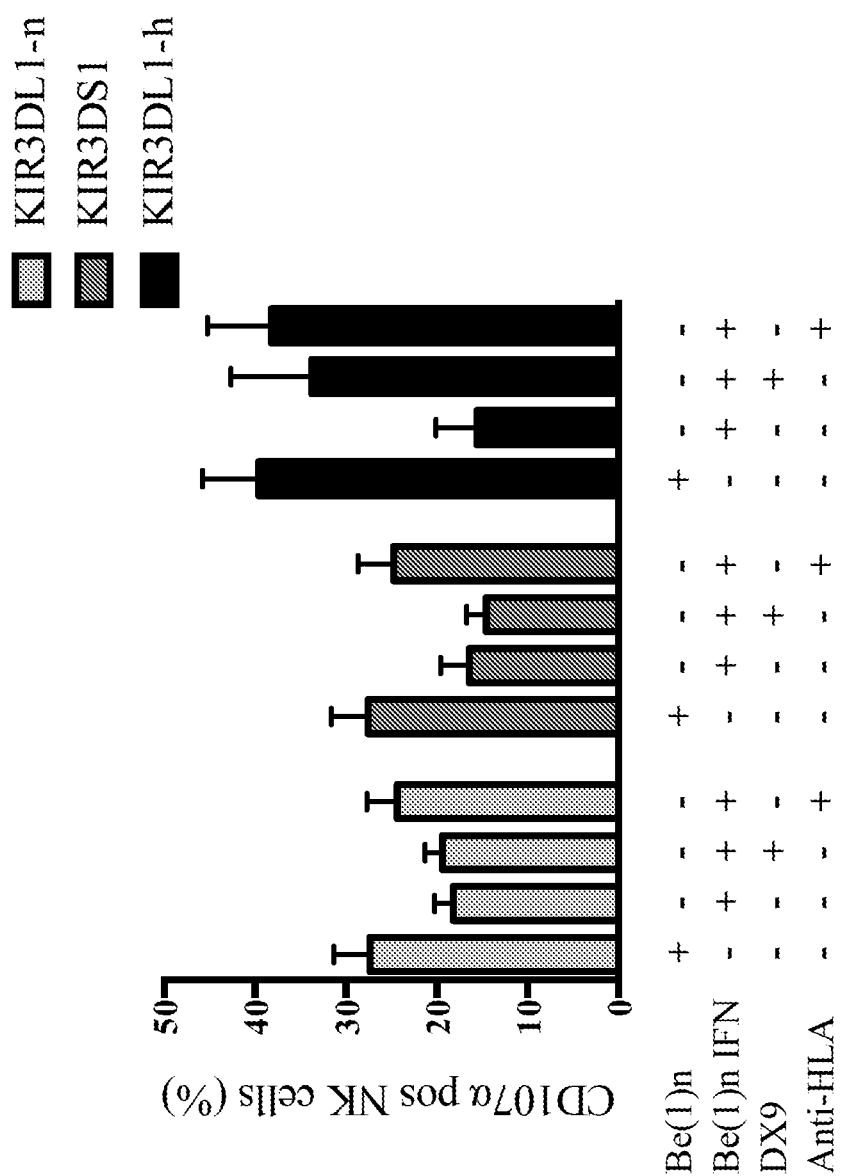
FIGS. 5A-5B depict NK activation against the Bw4+ BelN neuroblastoma (NB) tumor cell line.
Figure 5B:
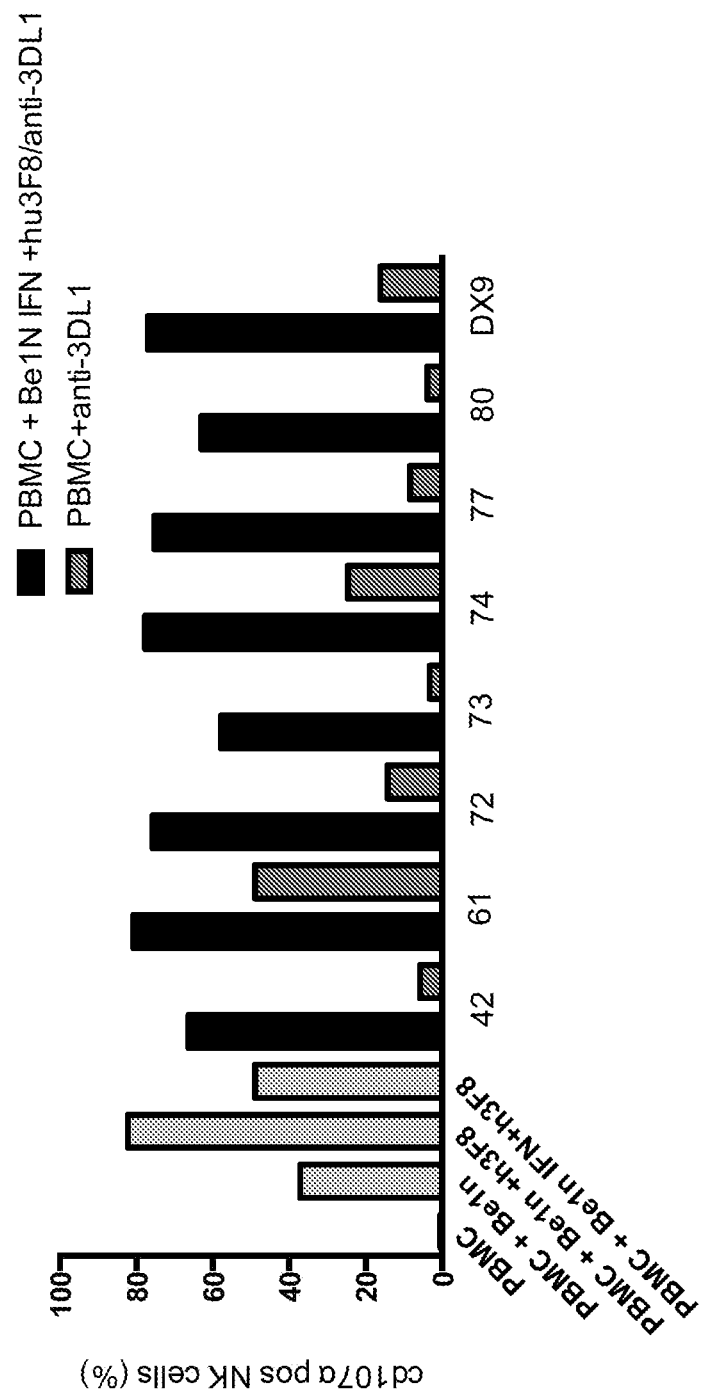

Anti-KIR3DL1 monoclonal antibodies can interfere with HLA-Bw4-mediated NK inhibition and permit antibody-directed cellular cytotoxicity (ADCC). NK cells are an important mediator of ADCC, a mechanism important to the success of therapeutic monoclonal antibodies, such as Rituximab and Cetuximab. Unfortunately, HLA class I expression on the target cancer cell can mediate inhibition of NK cells through KIR engagement and can thus significantly decrease the potency of NK cells to perform ADCC. To determine if the anti-KIR3DL1 antibodies can block HLA-mediated inhibition of ADCC by NK cells, an in vitro assay of NK activation by 3F8, a therapeutic monoclonal antibody to the ganglioside GD2 carried on the cell surface of neuroblastoma cells and other solid tumors, including melanoma, osteosarcoma, soft tissue sarcoma, small cell lung cancer, retinoblastoma, melanoma, and breast cancer stem cells, was used. The Fc portion of 3F8 binds the CD16 receptor on NK cells, leading to NK activation and CD107a mobilization. The neuroblastoma target cell line BE1N has low HLA expression at baseline but like most tumors readily upregulates HLA expression, including HLA-Bw4 expression, upon addition of low doses of the inflammatory cytokine IFN-γ. HLA-Bw4 expression on the NB tumor target inhibits NK cells with surface expression of KIR3DL1, despite strong activation signals from 3F8 (FIG. 5A). This inhibition does not occur for NK cells expressing the activating KIR3DS1 or the intracellular KIR3DL1*004 allele, neither of which binds the HLA-Bw4 ligand. Blocking the interaction between surface KIR3DL1 on the NK cell and HLA-Bw4 with either anti-HLA antibodies or the murine DX9 antibody interferes with KIR3DL1 inhibition, permitting NK activation by 3F8 in the presence of the NB target (FIG. 5A). Similar studies with the human IgG1 anti-KIR3DL1 antibodies were performed (FIG. 5B). These studies demonstrate that in comparison to the murine DX9, all antibody clones are capable of interfering with Bw4 inhibition, leading to disinhibition of NK cells and high NK activation (CD107a mobilization) ranging from 65-80% of NK cells. These data support the use of anti-KIR antibodies in combination with other therapeutic monoclonal antibodies to enhance ADCC in individuals who are HLA-Bw4+. The results demonstrate that the antibody agents of the present technology are useful for treating cancer in a subject in need thereof.

EQUIVALENTS

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure also includes embodiments in which more than one, or the entire group members are present in, employed in, or otherwise relevant to a given product or process. Furthermore, it is to be understood that the disclosure encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the present technology, or aspects of the present technology, is/are referred to as comprising particular elements, features, etc., certain embodiments of the present technology or aspects of the present technology consist, or consist essentially of, such elements, features, etc. For purposes of simplicity those embodiments have not in every case been specifically set forth in so many words herein. It should also be understood that any embodiment or aspect of the present technology can be explicitly excluded from the claims, regardless of whether the specific exclusion is recited in the specification. The publications, websites and other reference materials referenced herein to describe the background of the present technology and to provide additional detail regarding its practice are hereby incorporated by reference.

The invention claimed is:

1. An antibody or antigen binding fragment thereof comprising:
   (a) a heavy chain CDR1 sequence comprising SEQ ID NO:23, a heavy chain CDR2 sequence comprising SEQ ID NO:24, a heavy chain CDR3 sequence comprising SEQ ID NO:25, a light chain CDR1 sequence comprising SEQ ID NO:20, a light chain CDR2 sequence comprising SEQ ID NO:21, and a light chain CDR3 sequence comprising SEQ ID NO:22;
   (b) a heavy chain CDR1 sequence comprising SEQ ID NO:29, a heavy chain CDR2 sequence comprising SEQ ID NO:30, a heavy chain CDR3 sequence comprising SEQ ID NO:31, a light chain CDR1 sequence comprising SEQ ID NO:26, a light chain CDR2 sequence comprising SEQ ID NO:27 and a light chain CDR3 sequence comprising SEQ ID NO:28;
   (c) a heavy chain CDR1 sequence comprising SEQ ID NO:35, a heavy chain CDR2 sequence comprising SEQ ID NO:36, a heavy chain CDR3 sequence comprising SEQ ID NO:37, a light chain CDR1 sequence comprising SEQ ID NO: 32, a light chain CDR2 sequence comprising SEQ ID NO:33 and a light chain CDR3 sequence comprising SEQ ID NO:34;
   (d) a heavy chain CDR1 sequence comprising SEQ ID NO:41, a heavy chain CDR2 sequence comprising SEQ ID NO:42, a heavy chain CDR3 sequence comprising SEQ ID NO:43; a light chain CDR1 sequence comprising SEQ ID NO:38, a light chain CDR2 sequence comprising SEQ ID NO:39 and a light chain CDR3 sequence comprising SEQ ID NO:40;
   (e) a heavy chain CDR1 sequence comprising SEQ ID NO:47, a heavy chain CDR2 sequence comprising SEQ ID NO:48, a heavy chain CDR3 sequence comprising SEQ ID NO:49, a light chain CDR1 sequence comprising SEQ ID NO:44, a light chain CDR2 sequence comprising SEQ ID NO:45 and a light chain CDR3 sequence comprising SEQ ID NO:46;
   (f) a heavy chain CDR1 sequence comprising SEQ ID NO:53, a heavy chain CDR2 sequence comprising SEQ ID NO:54, a heavy chain CDR3 sequence comprising SEQ ID NO:55, a light chain CDR1 sequence comprising SEQ ID NO:50, a light chain CDR2 sequence comprising SEQ ID NO:51 and a light chain CDR3 sequence comprising SEQ ID NO:52; or
   (g) a heavy chain CDR1 sequence comprising SEQ ID NO:59, a heavy chain CDR2 sequence comprising SEQ ID NO:60, a heavy chain CDR3 sequence comprising SEQ ID NO:61, a light chain CDR1 sequence comprising SEQ ID NO:56, a light chain CDR2 sequence comprising SEQ ID NO:57 and a light chain CDR3 sequence comprising SEQ ID NO:58.

2. The antibody or antigen binding fragment of claim 1, wherein the antibody or antigen binding fragment comprises:
(a) a heavy chain variable region having a sequence selected from SEQ ID NOs: 7, 9, 11, 13, 15, 17, and 19; and
(b) a light chain variable region having a sequence selected from SEQ ID NOs: 6, 8, 10, 12, 14, 16, and 18.

3. The antibody or antigen binding fragment of claim 1, wherein the antibody or antigen binding fragment is monoclonal, humanized or chimeric.

4. The antibody or antigen binding fragment of claim 1, wherein the antibody or antigen binding fragment
blocks binding of human KIR3DL1 to HLA-Bw4;
activates natural killer cells;
binds to one or more alleles of KIR3DL1 selected from the group consisting of: *001, *002,*007, *015, *020, and *033; and/or
binds to an allele of KIR3DL1 with a $K_D$ of about 1 nM to 50 nM.

5. The antibody or antigen binding fragment of claim 1, wherein the antibody or antigen binding fragment is conjugated to a payload selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof.

6. The antibody or antigen binding fragment of claim 1, wherein the antibody or antigen binding fragment binds to an epitope of KIR3DL1 protein, wherein KIR3DL1 protein comprises an extracellular domain, wherein the epitope is a sequence present within the extracellular domain of KIR3DL1 protein, and wherein the extracellular domain of KIR3DL1 comprises a sequence selected from the group consisting of SEQ ID NOs: 1-5.

7. A nucleic acid molecule encoding the antibody or antigen binding fragment of claim 1.

8. A recombinant vector or a host cell comprising or the nucleic acid molecule of claim 7.

9. The host cell of claim 8, wherein the host cell is selected from the group consisting of a bacterial cell, a yeast cell, an insect cell a mammalian cell, an *E. coli* cell, a *P. pastoris* cell, a Sf9 cell, a COS cell, a HEK293 cell, a CHO cell, and a mammalian lymphocyte.

10. A pharmaceutical composition comprising:
(a) the antibody or antigen binding fragment of claim 1; and
(b) a pharmaceutically acceptable carrier.

11. A method of manufacturing the pharmaceutical composition of claim 10 by combining the antibody or antigen binding fragment, with the pharmaceutically acceptable carrier and formulating for administration to a subject.

12. A kit comprising the antibody or antigen binding fragment claim 1 and instructions for use.

13. A method of treating cancer in a subject in need thereof, comprising administering to the subject a therapeutically effective amount of a composition comprising the antibody or antigen binding fragment of claim 1.

14. The method of claim 13, wherein the subject has been diagnosed with or is at risk for developing cancer.

15. The method of claim 13, wherein the cancer is a leukemia, a solid tumor, acute myeloid leukemia (AML) or neuroblastoma.

16. The method of claim 13, wherein the subject expresses an allele of KIR3DL1.

17. The method of claim 16, wherein the allele of KIR3DL1 is selected from the group consisting of: *001, *016, *026, *027, *043, *052, *059, *060, *061, *064, *065, *067, *075, *002, *015, *008, *009, *020, *006, *017, *018, *022, *023, *024N, *025, *028, *029, *030, *031, *034, *035, *038, *042, *051, *054, *057, *062, *074, *076, *077, *005, *041, *044, *053, *007, *032, *068, *013, *010, *011, *012, *014, *045, *046, *047, *048, *049N, *050, *055, *058, *073, *004, *019, *021, *036, *037, *039, *040, *056, *063, *033 and *072.

18. The method of claim 16, wherein the allele of KIR3DL1 has been detected in a sample obtained from the subject.

19. The method of claim 16, wherein the subject has, is or will receive at least one additional therapy for the treatment of cancer, and optionally wherein the additional therapy is an anti-GD2 immunotherapy.

20. The method of claim 13, wherein the composition comprising the antibody or antigen binding fragment is administered orally, intranasally, parenterally, intravenously, intramuscularly, intraperitoneally, subcutaneously, rectally, intrathecally, intratumorally or topically.

\* \* \* \* \*

SEQUENCE LISTING

```
<160> NUMBER OF SEQ ID NOS: 66

<210> SEQ ID NO 1
<211> LENGTH: 319
<212> TYPE: PRT
<213> ORGANISM: Homo sapiens

<400> SEQUENCE: 1

His Met Gly Gly Gln Asp Lys Pro Phe Leu Ser Ala Trp Pro Ser Ala
1               5                   10                  15

Val Val Pro Arg Gly Gly His Val Thr Leu Arg Cys His Tyr Arg His
                20                  25                  30

Arg Phe Asn Asn Phe Met Leu Tyr Lys Glu Asp Arg Ile His Ile Pro
            35                  40                  45

Ile Phe His Gly Arg Ile Phe Gln Glu Ser Phe Asn Met Ser Pro Val
        50                  55                  60

Thr Thr Ala His Ala Gly Asn Tyr Thr Cys Arg Gly Ser His Pro His
65                  70                  75                  80

Ser Pro Thr Gly Trp Ser Ala Pro Ser Asn Pro Val Val Ile Met Val
                85                  90                  95

Thr Gly Asn His Arg Lys Pro Ser Leu Leu Ala His Pro Gly Pro Leu
                100                 105                 110

Val Lys Ser Gly Glu Arg Val Ile Leu Gln Cys Trp Ser Asp Ile Met
            115                 120                 125

Phe Glu His Phe Phe Leu His Lys Glu Gly Ile Ser Lys Asp Pro Ser
        130                 135                 140

Arg Leu Val Gly Gln Ile His Asp Gly Val Ser Lys Ala Asn Phe Ser
145                 150                 155                 160

Ile Gly Pro Met Met Leu Ala Leu Ala Gly Thr Tyr Arg Cys Tyr Gly
                165                 170                 175

Ser Val Thr His Thr Pro Tyr Gln Leu Ser Ala Pro Ser Asp Pro Leu
                180                 185                 190

Asp Ile Val Val Thr Gly Pro Tyr Glu Lys Pro Ser Leu Ser Ala Gln
            195                 200                 205

Pro Gly Pro Lys Val Gln Ala Gly Glu Ser Val Thr Leu Ser Cys Ser
        210                 215                 220

Ser Arg Ser Ser Tyr Asp Met Tyr His Leu Ser Arg Glu Gly Gly Ala
225                 230                 235                 240

His Glu Arg Arg Leu Pro Ala Val Arg Lys Val Asn Arg Thr Phe Gln
                245                 250                 255

Ala Asp Phe Pro Leu Gly Pro Ala Thr His Gly Gly Thr Tyr Arg Cys
            260                 265                 270

Phe Gly Ser Phe Arg His Ser Pro Tyr Glu Trp Ser Asp Pro Ser Asp
        275                 280                 285

Pro Leu Leu Val Ser Val Thr Gly Asn Pro Ser Ser Ser Trp Pro Ser
    290                 295                 300
```

```
Pro Thr Glu Pro Ser Ser Lys Ser Gly Asn Pro Arg His Leu His
305                 310                 315

<210> SEQ ID NO 2
<211> LENGTH: 317
<212> TYPE: PRT
<213> ORGANISM: Homo sapiens

<400> SEQUENCE: 2

His Val Gly Gly Gln Asp Lys Pro Phe Leu Ser Ala Trp Pro Ser Ala
1               5                   10                  15

Val Val Pro Arg Gly Gly His Val Thr Leu Arg Cys His Tyr Arg His
                20                  25                  30

Arg Phe Asn Asn Phe Met Leu Tyr Lys Glu Asp Arg Ile His Val Pro
            35                  40                  45

Ile Phe His Gly Arg Leu Phe Gln Glu Ser Phe Asn Met Ser Pro Val
        50                  55                  60

Thr Thr Ala His Ala Gly Asn Tyr Thr Cys Arg Gly Ser His Pro His
65                  70                  75                  80

Ser Pro Thr Gly Trp Ser Ala Pro Ser Asn Pro Val Val Ile Met Val
                85                  90                  95

Thr Gly Asn His Arg Lys Pro Ser Leu Leu Ala His Pro Gly Pro Leu
            100                 105                 110

Val Lys Ser Gly Glu Arg Val Ile Leu Gln Cys Trp Ser Asp Ile Met
        115                 120                 125

Phe Glu His Phe Phe Leu His Lys Glu Gly Ile Ser Lys Asp Pro Ser
130                 135                 140

Arg Leu Val Gly Gln Ile His Asp Gly Val Ser Lys Ala Asn Phe Ser
145                 150                 155                 160

Ile Gly Pro Met Met Leu Ala Leu Ala Gly Thr Tyr Arg Cys Tyr Gly
                165                 170                 175

Ser Val Thr His Thr Pro Tyr Gln Leu Ser Ala Pro Ser Asp Pro Leu
            180                 185                 190

Asp Ile Val Val Thr Gly Pro Tyr Glu Lys Pro Ser Leu Ser Ala Gln
        195                 200                 205

Pro Gly Pro Lys Val Gln Ala Gly Glu Ser Val Thr Leu Ser Cys Ser
210                 215                 220

Ser Arg Ser Ser Tyr Asp Met Tyr His Leu Ser Arg Glu Arg Gly Ala
225                 230                 235                 240

His Glu Arg Arg Leu Pro Ala Val Arg Lys Val Asn Arg Thr Phe Gln
                245                 250                 255

Ala Asp Phe Pro Leu Gly Pro Ala Thr His Gly Gly Thr Tyr Arg Cys
            260                 265                 270

Phe Gly Ser Phe Arg His Ser Pro Tyr Glu Trp Ser Asp Pro Ser Asp
        275                 280                 285

Pro Leu Leu Val Ser Val Thr Gly Asn Pro Ser Ser Ser Trp Pro Ser
290                 295                 300

Pro Thr Glu Pro Ser Ser Lys Ser Gly Asn Pro Arg His
305                 310                 315

<210> SEQ ID NO 3
<211> LENGTH: 317
<212> TYPE: PRT
<213> ORGANISM: Homo sapiens
```

<400> SEQUENCE: 3

```
His Val Gly Gly Gln Asp Lys Pro Phe Leu Ser Ala Trp Pro Ser Ala
1               5                   10                  15

Val Val Pro Arg Gly Gly His Val Thr Leu Arg Cys His Tyr Arg His
            20                  25                  30

Arg Phe Asn Asn Phe Met Leu Tyr Lys Glu Asp Arg Ile His Val Pro
        35                  40                  45

Ile Phe His Gly Arg Leu Phe Gln Glu Ser Phe Asn Met Ser Pro Val
    50                  55                  60

Thr Thr Ala His Ala Gly Asn Tyr Thr Cys Arg Gly Ser His Pro His
65                  70                  75                  80

Ser Pro Thr Gly Trp Ser Ala Pro Ser Asn Pro Val Val Ile Met Val
                85                  90                  95

Thr Gly Asn His Arg Lys Pro Ser Leu Leu Ala His Pro Gly Pro Leu
            100                 105                 110

Val Lys Ser Gly Glu Arg Val Ile Leu Gln Cys Trp Ser Asp Ile Met
        115                 120                 125

Phe Glu His Phe Phe Leu His Lys Glu Gly Ile Ser Lys Asp Pro Ser
130                 135                 140

Arg Leu Val Gly Gln Ile His Asp Gly Val Ser Lys Ala Asn Phe Ser
145                 150                 155                 160

Ile Gly Pro Met Met Leu Ala Leu Ala Gly Thr Tyr Arg Cys Tyr Gly
                165                 170                 175

Ser Val Thr His Thr Pro Tyr Gln Leu Ser Ala Pro Ser Asp Pro Leu
            180                 185                 190

Asp Ile Val Val Thr Gly Pro Tyr Glu Lys Pro Ser Leu Ser Ala Gln
        195                 200                 205

Pro Gly Pro Lys Val Gln Ala Gly Glu Ser Val Thr Leu Ser Cys Ser
    210                 215                 220

Ser Arg Ser Ser Tyr Asp Met Tyr His Leu Ser Arg Glu Arg Gly Ala
225                 230                 235                 240

His Glu Arg Arg Leu Pro Ala Val Arg Lys Val Asn Arg Thr Phe Gln
                245                 250                 255

Ala Asp Phe Pro Leu Gly Pro Ala Thr His Gly Gly Thr Tyr Arg Cys
            260                 265                 270

Phe Gly Ser Phe Arg His Ser Pro Tyr Glu Trp Ser Asp Pro Ser Asp
        275                 280                 285

Pro Leu Leu Val Ser Val Thr Gly Asn Pro Ser Ser Ser Trp Pro Ser
    290                 295                 300

Pro Thr Glu Pro Ser Ser Lys Ser Gly Asn Pro Arg His
305                 310                 315
```

<210> SEQ ID NO 4
<211> LENGTH: 318
<212> TYPE: PRT
<213> ORGANISM: Homo sapiens

<400> SEQUENCE: 4

```
His Val Gly Gly Gln Asp Lys Pro Phe Leu Ser Ala Trp Pro Ser Ala
1               5                   10                  15

Val Val Pro Arg Gly Gly His Val Thr Leu Arg Cys His Tyr Arg His
            20                  25                  30

Arg Phe Asn Asn Phe Met Leu Tyr Lys Glu Asp Arg Ile His Val Pro
        35                  40                  45
```

Ile Phe His Gly Arg Leu Phe Gln Glu Ser Phe Asn Met Ser Pro Val
 50                  55                  60

Thr Thr Ala His Ala Gly Asn Tyr Thr Cys Arg Gly Ser His Pro His
 65                  70                  75                  80

Ser Pro Thr Gly Trp Ser Ala Pro Ser Asn Pro Val Val Ile Met Val
                 85                  90                  95

Thr Gly Asn His Arg Lys Pro Ser Leu Leu Ala His Pro Gly Pro Leu
            100                 105                 110

Val Lys Ser Gly Glu Arg Val Ile Leu Gln Cys Trp Ser Asp Ile Met
        115                 120                 125

Phe Glu His Phe Leu His Lys Glu Gly Ile Ser Lys Asp Pro Ser
130                 135                 140

Ser Leu Val Gly Gln Ile His Asp Gly Val Ser Lys Ala Asn Phe Ser
145                 150                 155                 160

Ile Gly Pro Met Met Leu Ala Leu Ala Gly Thr Tyr Arg Cys Tyr Gly
                165                 170                 175

Ser Val Thr His Thr Pro Tyr Gln Leu Ser Ala Pro Ser Asp Pro Leu
            180                 185                 190

Asp Ile Val Val Thr Gly Pro Tyr Glu Lys Pro Ser Leu Ser Ala Gln
        195                 200                 205

Pro Gly Pro Lys Val Gln Ala Gly Glu Ser Val Thr Leu Ser Cys Ser
210                 215                 220

Ser Arg Ser Ser Tyr Asp Met Tyr His Leu Ser Arg Glu Gly Gly Ala
225                 230                 235                 240

His Glu Arg Arg Leu Pro Ala Val Arg Lys Val Asn Arg Thr Phe Gln
                245                 250                 255

Ala Asp Phe Pro Leu Gly Pro Ala Thr His Gly Gly Thr Tyr Arg Cys
            260                 265                 270

Phe Gly Ser Phe Arg His Ser Pro Tyr Glu Trp Ser Asp Pro Ser Asp
        275                 280                 285

Pro Leu Leu Val Ser Val Thr Gly Asn Pro Ser Ser Ser Trp Pro Ser
290                 295                 300

Pro Thr Glu Pro Ser Ser Lys Ser Gly Asn Pro Arg His Leu
305                 310                 315

<210> SEQ ID NO 5
<211> LENGTH: 319
<212> TYPE: PRT
<213> ORGANISM: Homo sapiens

<400> SEQUENCE: 5

His Val Gly Gly Gln Asp Lys Pro Phe Leu Ser Ala Trp Pro Ser Ala
 1               5                  10                  15

Val Val Pro Arg Gly Gly His Val Thr Leu Arg Cys His Tyr Arg His
                 20                  25                  30

Arg Phe Asn Asn Phe Met Leu Tyr Lys Glu Asp Arg Ile His Val Pro
            35                  40                  45

Ile Phe His Gly Arg Leu Phe Gln Glu Ser Phe Asn Met Ser Pro Val
        50                  55                  60

Thr Thr Ala His Ala Gly Asn Tyr Thr Cys Arg Gly Ser His Pro His
 65                  70                  75                  80

Ser Pro Thr Gly Trp Ser Ala Pro Ser Asn Pro Val Val Ile Met Val
                 85                  90                  95

```
Thr Gly Asn His Arg Lys Pro Ser Leu Leu Ala His Pro Gly Pro Leu
            100                 105                 110

Val Lys Ser Gly Glu Arg Val Ile Leu Gln Cys Trp Ser Asp Ile Met
        115                 120                 125

Phe Glu His Phe Phe Leu His Lys Gly Ile Ser Glu Asp Pro Ser
130                 135                 140

Arg Leu Val Gly Gln Ile His Asp Gly Val Ser Lys Ala Asn Phe Ser
145                 150                 155                 160

Ile Gly Pro Met Met Leu Ala Leu Ala Gly Thr Tyr Arg Cys Tyr Gly
                165                 170                 175

Ser Val Thr His Thr Pro Tyr Gln Leu Ser Ala Pro Ser Asp Pro Leu
            180                 185                 190

Asp Ile Val Val Thr Gly Pro Tyr Glu Lys Pro Ser Leu Ser Ala Gln
        195                 200                 205

Pro Gly Pro Lys Val Gln Ala Gly Glu Ser Val Thr Leu Ser Cys Ser
    210                 215                 220

Ser Arg Ser Ser Tyr Asp Met Tyr His Leu Ser Arg Glu Gly Gly Ala
225                 230                 235                 240

His Glu Arg Arg Leu Pro Ala Val Arg Lys Val Asn Arg Thr Phe Gln
                245                 250                 255

Ala Asp Phe Pro Leu Gly Pro Ala Thr His Gly Gly Thr Tyr Arg Cys
            260                 265                 270

Phe Gly Ser Phe Arg His Ser Pro Tyr Glu Trp Ser Asp Pro Ser Asp
        275                 280                 285

Pro Leu Leu Val Ser Val Thr Gly Asn Pro Ser Ser Ser Trp Pro Ser
    290                 295                 300

Pro Thr Glu Pro Ser Ser Lys Ser Gly Asn Pro Arg His Leu His
305                 310                 315

<210> SEQ ID NO 6
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Asn Thr Leu Val Phe Gly Thr Gly Thr Lys Val Thr Val Leu Gly
            100                 105                 110

<210> SEQ ID NO 7
<211> LENGTH: 112
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Asp Leu Phe Tyr Trp Gly Gln Gly Thr Leu Val Thr Val Ser Ser
            100                 105                 110

<210> SEQ ID NO 8
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asn Phe Met Leu Thr Gln Pro Leu Ser Val Ser Glu Ser Pro Gly Lys
1               5                   10                  15

Thr Val Thr Ile Ser Cys Thr Ala Asn Gly Gly Ser Leu Ala Ser Lys
                20                  25                  30

Tyr Val Gln Trp Phe Gln Gln Arg Pro Gly Ser Ser Pro Thr Thr Val
            35                  40                  45

Ile Tyr Asp Asp Asn Leu Arg Pro Ser Gly Val Pro Asp Arg Phe Ser
        50                  55                  60

Gly Ser Ile Asp Thr Ser Ser Asn Ser Ala Ala Leu Thr Ile Ser Gly
65                  70                  75                  80

Leu Lys Thr Glu Asp Glu Ala Asp Tyr Tyr Cys Gln Ser Tyr Asp Asn
                85                  90                  95

Ser Ser Val Phe Gly Gly Gly Thr Lys Leu Thr Val Leu Gly
            100                 105                 110

<210> SEQ ID NO 9
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45
```

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Ser Leu Arg Tyr Phe Glu Trp Pro Ile Asp Tyr Trp Gly Gln
            100                 105                 110

Gly Thr Leu Val Thr Val Ser Ser
            115                 120

<210> SEQ ID NO 10
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Leu Pro Val Leu Thr Gln Pro Ser Ile Ser Gly Ala Pro Arg Gln
1               5                   10                  15

Arg Val Thr Ile Ser Cys Ser Gly Ala Arg Ser Asn Ile Gly Asn Asn
                20                  25                  30

Ala Val Asn Trp Tyr Gln Gln Val Pro Gly Glu Ala Pro Lys Leu Leu
            35                  40                  45

Ile Phe Tyr Asp Asp Gln Gln Pro Ser Gly Ile Ser Gly Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu Gly
            100                 105                 110

<210> SEQ ID NO 11
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Val Gln Ser Gly Gly Gly Val Val Arg Ser Gly Gly
1               5                   10                  15

Ser Leu Arg Leu Thr Cys Ala Ala Ser Gly Phe Thr Phe Gly Asp Tyr
                20                  25                  30

Gly Met Ser Trp Val Arg Gln Ala Pro Gly Lys Gly Leu Glu Trp Val
            35                  40                  45

Ser Gly Ile Asn Trp Asn Gly Gly Thr Gly Tyr Ala Asp Ser Val
        50                  55                  60

Lys Gly Arg Phe Thr Ile Ser Arg Asp Asn Ala Lys Asp Ser Leu Tyr
65                  70                  75                  80

Leu Gln Met Asn Ser Leu Arg Ala Glu Asp Thr Ala Leu Tyr Tyr Cys
                85                  90                  95

Ala Arg Val Trp Gly Cys Gly Ser Thr Thr Cys Tyr Glu Gly Ala Asp
            100                 105                 110

Asp Ala Phe Asp Ile Trp Gly Gln Gly Thr Met Val Thr Val Ser Ser
            115                 120                 125

<210> SEQ ID NO 12
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Val Val Met Thr Gln Ser Pro Leu Ser Leu Pro Val Thr Leu Gly
1               5                   10                  15

Gln Pro Ala Ser Ile Ser Cys Arg Ser Thr Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Gly Val Ser Asn Arg Asp Phe Gly Val Pro
    50                  55                  60

Asp Arg Phe Ser Ala Ser Gly Ser Gly Thr Asp Phe Thr Leu Lys Ile
65                  70                  75                  80

Asn Arg Val Glu Ala Glu Asp Val Gly Val Tyr Tyr Cys Met Gln Gly
                85                  90                  95

Thr His Trp Pro Leu Thr Phe Gly Gln Gly Thr Lys Val Glu Ile Lys
            100                 105                 110

Arg

<210> SEQ ID NO 13
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Arg Glu Gln Leu Trp Leu Asp Gly Met Asp Val Trp Gly
            100                 105                 110

Gln Gly Thr Thr Val Thr Val Ser Ser
        115                 120

<210> SEQ ID NO 14
<211> LENGTH: 111
<212> TYPE: PRT
<213> ORGANISM: Artificial Sequence
<220> FEATURE:

<223> OTHER INFORMATION: Description of Artificial Sequence: Synthetic
     polypeptide

<400> SEQUENCE: 14

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Val Gly Asn Asn
            20                  25                  30

Tyr Val Ser Trp Tyr Gln Gln Val Pro Gly Thr Ala Pro Lys Leu Leu
        35                  40                  45

Ile Tyr Asp Asn Asn Arg Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Asn Ser Leu
                85                  90                  95

Arg Val Glu Leu Phe Gly Gly Gly Thr Lys Val Thr Val Leu Gly
            100                 105                 110

<210> SEQ ID NO 15
<211> LENGTH: 116
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Ser Phe His Leu Asp Gly Trp Gly Gln Gly Thr Leu Val
            100                 105                 110

Thr Val Ser Ser
        115

<210> SEQ ID NO 16
<211> LENGTH: 109
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 16

Ser Tyr Glu Leu Thr Gln Pro Pro Ser Val Ser Val Ala Pro Gly Gln
1               5                   10                  15

Ala Ala Thr Ile Thr Cys Ala Gly Asp Asn Ile Glu Ser Lys Ser Val
            20                  25                  30

```
Asn Trp Tyr Gln Gln Lys Pro Gly Gln Ala Pro Val Leu Val Val Tyr
        35                  40                  45

Asp Asp Thr Val Arg Pro Ser Gly Ile Pro Glu Arg Phe Ser Gly Ser
 50                  55                  60

Asn Ser Gly Asn Pro Ala Thr Leu Thr Ile Ser Arg Ser Glu Ala Gly
 65                  70                  75                  80

Asp Glu Ala Asp Tyr Tyr Cys Gln Val Trp Asp Asn Arg Arg Asp His
                 85                  90                  95

Val Val Phe Gly Gly Gly Thr Lys Val Thr Val Leu Gly
                100                 105

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Val Glu Thr Gly Gly Gly Leu Val Lys Pro Gly Gly
 1               5                  10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
        35                  40                  45

Ser Tyr Ile Ser Ser Ser Ser Tyr Thr Asn Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Ile Ala Ala Ala Asp Ala Phe Asp Ile Trp Gly Gln
                100                 105                 110

Gly Thr Met Val Thr Val Ser Ser
        115                 120

<210> SEQ ID NO 18
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Ala Val Val Thr Gln Glu Pro Ser Leu Thr Val Ser Pro Gly Gly
 1               5                  10                  15

Thr Val Thr Leu Thr Cys Gly Ser Ser Thr Gly Ala Val Thr Ser Gly
                20                  25                  30

His Tyr Pro Tyr Trp Phe Gln Gln Lys Pro Gly Gln Ala Pro Arg Thr
        35                  40                  45

Leu Ile Tyr Glu Thr Ser Asn Lys Tyr Ser Trp Thr Pro Ala Arg Phe
 50                  55                  60

Ser Gly Ser Leu Leu Gly Gly Lys Ala Ala Leu Thr Leu Ser Gly Ala
 65                  70                  75                  80

Gln Pro Glu Asp Glu Ala Glu Tyr His Cys Phe Leu Ser Tyr Ser Gly
                 85                  90                  95
```

```
Thr Val Val Phe Gly Gly Gly Thr Lys Leu Thr Val Leu Gly
            100                 105                 110
```

<210> SEQ ID NO 19
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Arg Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
            85                  90                  95

Ala Arg Tyr Gly Asp Trp Gly Gln Gly Thr Leu Val Thr Val Ser Ser
            100                 105                 110
```

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Ser Ser Asp Val Gly Gly Tyr Asn Tyr
1               5
```

<210> SEQ ID NO 21
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

```
Asp Val Ser
1
```

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

```
Ser Ser Tyr Thr Ser Ser Asn Thr Leu Val
1               5                   10
```

```
<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Tyr Thr Phe Thr Gly Tyr Tyr
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ile Asn Pro Asn Ser Gly Gly Thr
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Asp Leu Phe Tyr
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Gly Ser Leu Ala Ser Lys Tyr
1               5

<210> SEQ ID NO 27
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Asp Asn
1

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 28

Gln Ser Tyr Asp Asn Ser Ser Val Val
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Phe Thr Phe Asp Asp Tyr Ala
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ile Ser Trp Asn Ser Gly Ser Ile
1               5

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Ser Ser Leu Arg Tyr Phe Glu Trp Pro Ile Asp Tyr
1               5                   10

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Ser Asn Ile Gly Asn Asn Ala
1               5

<210> SEQ ID NO 33
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Tyr Asp Asp
1

<210> SEQ ID NO 34
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Ala Trp Asp Asp Ser Leu Asn Gly
1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Phe Thr Phe Gly Asp Tyr Gly
1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ile Asn Trp Asn Gly Gly Gly Thr
1               5

<210> SEQ ID NO 37
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Arg Val Trp Gly Cys Gly Ser Thr Thr Cys Tyr Glu Gly Ala Asp
1               5                   10                  15

Asp Ala Phe Asp Ile
            20

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Ser Leu Val His Ser Asp Gly Asn Thr Tyr
1               5                   10

<210> SEQ ID NO 39
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 39

Gly Val Ser
1

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Met Gln Gly Thr His Trp Pro Leu Thr
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Tyr Ser Phe Thr Ser Tyr Trp
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ile Tyr Pro Gly Asp Ser Asp Thr
1               5

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Arg Gly Arg Glu Gln Leu Trp Leu Asp Gly Met Asp Val
1               5                   10

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ser Ser Asn Val Gly Asn Asn Tyr
1               5

<210> SEQ ID NO 45
<211> LENGTH: 3
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 45

Asp Asn Asn
1

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Thr Trp Asp Asn Ser Leu Arg Val Glu Leu
1               5                   10

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Gly Thr Phe Ser Ser Tyr Ala
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Met Asn Pro Asn Ser Gly Asn Thr
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Arg Tyr Ser Phe His Leu Asp Gly
1               5

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asn Ile Glu Ser Lys Ser
1               5

```
<210> SEQ ID NO 51
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Asp Thr
1

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Val Trp Asp Asn Arg Arg Asp His Val Val
1               5                   10

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Phe Thr Phe Ser Asp Tyr Tyr
1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ile Ser Ser Ser Ser Ser Tyr Thr
1               5

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Arg Glu Gly Ile Ala Ala Asp Ala Phe Asp Ile
1               5                   10

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 56

Thr Gly Ala Val Thr Ser Gly His Tyr
1               5

<210> SEQ ID NO 57
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Glu Thr Ser
1

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Phe Leu Ser Tyr Ser Gly Thr Val Val
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Tyr Thr Phe Thr Gly Tyr Tyr
1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ile Asn Pro Asn Ser Gly Gly Thr
1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Arg Tyr Gly Asp
1               5

<210> SEQ ID NO 62
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Y, F, or G
<220> FEATURE:
<221> NAME/KEY: MOD_RES
<222> LOCATION: (3)..(3)
<223> OTHER INFORMATION: T or S
<220> FEATURE:
<221> NAME/KEY: MOD_RES
<222> LOCATION: (5)..(5)
<223> OTHER INFORMATION: T, S, D, or G
<220> FEATURE:
<221> NAME/KEY: MOD_RES
<222> LOCATION: (6)..(6)
<223> OTHER INFORMATION: G, S, or D
<220> FEATURE:
<221> NAME/KEY: MOD_RES
<222> LOCATION: (8)..(8)
<223> OTHER INFORMATION: Y, W, A, or G

<400> SEQUENCE: 62

Gly Xaa Xaa Phe Xaa Xaa Tyr Xaa
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: I or M
<220> FEATURE:
<221> NAME/KEY: MOD_RES
<222> LOCATION: (2)..(2)
<223> OTHER INFORMATION: N, S, or Y
<220> FEATURE:
<221> NAME/KEY: MOD_RES
<222> LOCATION: (3)..(3)
<223> OTHER INFORMATION: P, W, or S
<220> FEATURE:
<221> NAME/KEY: MOD_RES
<222> LOCATION: (4)..(4)
<223> OTHER INFORMATION: N, G, or S
<220> FEATURE:
<221> NAME/KEY: MOD_RES
<222> LOCATION: (5)..(5)
<223> OTHER INFORMATION: S, D, or G
<220> FEATURE:
<221> NAME/KEY: MOD_RES
<222> LOCATION: (6)..(6)
<223> OTHER INFORMATION: G or S
<220> FEATURE:
<221> NAME/KEY: MOD_RES
<222> LOCATION: (7)..(7)
<223> OTHER INFORMATION: G, Y, D, S, or N
<220> FEATURE:
<221> NAME/KEY: MOD_RES
<222> LOCATION: (8)..(8)
<223> OTHER INFORMATION: T or I

<400> SEQUENCE: 63

Xaa Xaa Xaa Xaa Xaa Xaa Xaa Xaa
1               5
```

```
<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Gly Gly Gly Ser Gly Gly Gly Gly Ser Gly Gly Gly Gly Ser
1               5                   10                  15

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Gly Gly Gly Ser
1               5

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 66

Gly Gly Gly Gly Ser
1               5
```